US008239211B2

(12) United States Patent
Feldman et al.

(10) Patent No.: US 8,239,211 B2
(45) Date of Patent: Aug. 7, 2012

(54) GLOBAL INVESTMENT GRADE FOR NATURAL AND SYNTHETIC GEMS USED IN FINANCIAL INVESTMENTS AND COMMERCIAL TRADING AND METHOD OF CREATING STANDARDIZED BASKETS OF GEMS TO BE USED IN FINANCIAL AND COMMERCIAL PRODUCTS

(75) Inventors: Victor Feldman, Glencoe, IL (US);
Sharon Karsten, Chicago, IL (US);
Daniel Gramza, Evanston, IL (US);
David W So, New York, NY (US);
Andrew J Feldman, Chicago, IL (US)

(73) Assignee: Gemshares LLC, Chicago, IL (US)

( * ) Notice: Subject to any disclaimer, the term of this patent is extended or adjusted under 35 U.S.C. 154(b) by 532 days.

(21) Appl. No.: 12/413,276

(22) Filed: Mar. 27, 2009

(65) Prior Publication Data
US 2009/0248591 A1 Oct. 1, 2009

Related U.S. Application Data

(60) Provisional application No. 61/072,326, filed on Mar. 27, 2008, provisional application No. 61/089,204, filed on Aug. 15, 2008.

(51) Int. Cl.
*G06Q 10/00* (2012.01)

(52) U.S. Cl. ........................................................ 705/1.1
(58) Field of Classification Search .................. None
See application file for complete search history.

(56) References Cited

U.S. PATENT DOCUMENTS
2006/0074588 A1  4/2006  Blodgett et al.
2006/0164623 A1  7/2006  Wagner et al.

FOREIGN PATENT DOCUMENTS
WO      0133316 A2   5/2001

*Primary Examiner* — Jonathan Ouellette
(74) *Attorney, Agent, or Firm* — Vedder Price PC

(57) ABSTRACT

A process to create a fungible global standard for diamonds and gemstones. The process involves grouping diamonds in an investment standard according to their gemological, proportional, optical and light behavior characteristics. Diamonds that conform to the investment grade standard are interchangeable within a specific size range according to an equivalent monetary bundling process. Diamonds subjected to the standard conform to a holistic set of gemological, proportional, optical and light characteristic requirements that enables diamonds to be classified into a extraordinarily homogeneous, visually indistinguishable and highly fungible group which can be used to create baskets of diamonds to form an index/benchmark for diamond pricing, financial instruments, and a standard that can be used for certifying diamonds as investment grade to insure quality.

12 Claims, 27 Drawing Sheets

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | D | 28 | 60 | 94 | 99 | 75 | 74 | 430 |
| | E | 22 | 58 | 105 | 108 | 94 | 81 | 468 |
| | F | 30 | 39 | 126 | 153 | 146 | 78 | 572 |
| | G | 34 | 67 | 92 | 175 | 145 | 131 | 644 |
| | H | 13 | 23 | 35 | 78 | 88 | 89 | 326 |
| | I | 1 | 10 | 12 | 53 | 84 | 46 | 206 |
| | J | 1 | 7 | 5 | 17 | 48 | 41 | 119 |
| | Total | 129 | 264 | 469 | 683 | 680 | 540 | 2,785 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.50-0.59 | D | 1.0% | 2.2% | 3.4% | 3.6% | 2.7% | 2.7% | 15.6% |
| | E | 0.8% | 2.1% | 3.8% | 3.9% | 3.4% | 2.9% | 16.9% |
| | F | 1.1% | 1.4% | 4.6% | 5.5% | 5.3% | 2.8% | 20.7% |
| | G | 1.2% | 2.4% | 3.3% | 6.3% | 5.2% | 4.7% | 23.3% |
| | H | 0.5% | 0.8% | 1.3% | 2.8% | 3.2% | 3.2% | 11.8% |
| | I | 0.0% | 0.4% | 0.4% | 1.9% | 3.0% | 1.7% | 7.5% |
| | J | 0.0% | 0.3% | 0.3% | 0.6% | 1.7% | 1.5% | 4.3% |
| | Total | 4.7% | 9.5% | 17.0% | 24.7% | 24.6 | 19.5% | 100.0% |

| Component | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | D | | | | | | | |
| | E | | | 1 | 1 | | | |
| | F | | | 1 | 1 | 1 | | |
| | G | | | | 2 | 1 | 1 | |
| | H | | | | | | | |
| | I | | | | | | | |
| | J | | | | | | | |
| | Total | | | | | | 9 | 15% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 0.53 | D | $7,600 | $6,100 | $5,500 | $4,500 | $4,100 | $3,500 |
| | E | $6,000 | $5,500 | $5,100 | $4,200 | $3,800 | $3,200 |
| | F | $5,500 | $5,100 | $4,800 | $4,000 | $3,600 | $2,900 |
| | G | $5,100 | $4,600 | $4,300 | $3,800 | $3,300 | $2,700 |
| | H | $4,500 | $4,000 | $3,600 | $3,300 | $2,900 | $2,500 |
| | I | $3,700 | $3,300 | $3,000 | $2,700 | $2,500 | $2,200 |
| | J | $2,900 | $2,700 | $2,600 | $2,300 | $2,200 | $2,000 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $2,703 | $2,226 | $0 | $0 | | | |
| | F | $0 | $0 | $2,544 | $2,120 | $1,908 | $0 | | | |
| | G | $0 | $0 | $0 | $4,028 | $1,749 | $1,431 | | | |
| | H | $0 | $0 | $0 | $0 | $0 | $0 | | | |
| | I | $0 | $0 | $0 | $0 | $0 | $0 | | | |
| | J | $0 | $0 | $0 | $0 | $0 | $0 | | | |
| | Total | | | | | | | $18,709 | 4.77 | 9 |

FIG. 5

| Count | Clarity | | | | | | |
|---|---|---|---|---|---|---|---|
| Range | Color | 1-IF/FL | 2-VVS1 | 3-VVS2 | 4-VS1 | 5-VS2 | 6-SI1 | Total |
| 0.70-0.83 | D | 12 | 14 | 29 | 74 | 90 | 133 | 352 |
| | E | 9 | 41 | 51 | 111 | 182 | 253 | 647 |
| | F | 11 | 53 | 68 | 126 | 185 | 270 | 713 |
| | G | 26 | 50 | 68 | 119 | 185 | 211 | 659 |
| | H | 16 | 41 | 31 | 115 | 134 | 177 | 514 |
| | I | 8 | 39 | 46 | 96 | 159 | 156 | 504 |
| | J | 11 | 9 | 17 | 58 | 74 | 73 | 242 |
| | Total | 93 | 247 | 310 | 699 | 1,009 | 1,273 | 3.631 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.70-0.83 | D | 0.3% | 0.4% | 0.8% | 2.0% | 2.5% | 3.7% | 9.7% |
| | E | 0.2% | 1.1% | 1.4% | 3.15 | 5.0% | 7.0% | 17.8% |
| | F | 0.3% | 1.5% | 1.9% | 3.5% | 5.1% | 7.4% | 19.6% |
| | G | 0.7% | 1.4% | 1.9% | 3.3% | 5.1% | 5.8% | 18.1% |
| | H | 0.4% | 1.1% | 0.9% | 3.2% | 3.7% | 4.9% | 14.2% |
| | I | 0.2% | 1.1% | 1.3% | 2.6% | 4.4% | 4.3% | 13.9% |
| | J | 0.3% | 0.2% | 0.55 | 1.6% | 2.0% | 2.0% | 6.7% |
| | Total | 2.63% | 6.85 | 8.55 | 19.3% | 27.8% | 35.1% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.70-0.83 | | | | | 1 | 1 | | |
| | | | | 1 | 1 | 1 | 1 | |
| | | | 1 | 1 | 1 | 1 | 1 | |
| | | | | 1 | 1 | 1 | | |
| | Total | | | | | | | 12 | 20% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 0.74 | D | $9,000 | $7,100 | $6,500 | $5,800 | $5,300 | $4,700 |
| | E | $7,000 | $6,600 | $5,900 | $5,400 | $5,000 | $4,500 |
| | F | $6,500 | $6,100 | $5,500 | $5,100 | $4,700 | $4,200 |
| | G | $6,000 | $5,500 | $5,100 | $4,700 | $4,400 | $3,900 |
| | H | $5,400 | $4,900 | $4,500 | $4,200 | $4,000 | $3,600 |
| | I | $4,500 | $4,200 | $4,000 | $3,800 | $3,600 | $3,300 |
| | J | $3,500 | $3,400 | $3,300 | $3,100 | $3,000 | $2,900 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.70-0.83 | D | $0 | $0 | $0 | $0 | $0 | $0 | | | |
| | E | $0 | $0 | $0 | $3,996 | $3,700 | $0 | | | |
| | F | $0 | $0 | $0 | $3,774 | $3,478 | $3,108 | | | |
| | G | $0 | $0 | $0 | $3,478 | $3,256 | $2,886 | | | |
| | H | $0 | $0 | $0 | $3,108 | $2,960 | $2,664 | | | |
| | I | $0 | $0 | $0 | $0 | $2,684 | $0 | | | |
| | J | $0 | $0 | $0 | $0 | $0 | $0 | | | |
| | Total | | | | | | | $39,072 | 8.88 | 12 |

FIG. 5
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.00-1.19 | D | 27 | 17 | 64 | 74 | 78 | 84 | 344 |
| | E | 24 | 47 | 93 | 130 | 185 | 151 | 630 |
| | F | 80 | 106 | 162 | 213 | 368 | 231 | 1,160 |
| | G | 41 | 53 | 97 | 243 | 424 | 363 | 1,221 |
| | H | 14 | 9 | 15 | 116 | 328 | 429 | 821 |
| | I | 1 | 6 | 11 | 74 | 108 | 286 | 486 |
| | J | 4 | 13 | 20 | 56 | 121 | 170 | 384 |
| | Total | 191 | 251 | 462 | 906 | 1,522 | 1,714 | 5,046 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 1.00-1.19 | D | 0.5% | 0.3% | 1.3% | 1.5% | 1.5% | 1.7% | 6.8% |
| | E | 0.5% | 0.9% | 1.8% | 2.8% | 3.7% | 3.0% | 12.5% |
| | F | 1.6% | 2.1% | 3.2% | 4.2% | 7.3% | 4.6% | 23.0% |
| | G | 0.8% | 1.1% | 1.9% | 4.8% | 8.4% | 7.2% | 24.2% |
| | H | 0.3% | 0.2% | 0.3% | 2.3% | 4.7% | 8.5% | 16.3% |
| | I | 0.0% | 0.1% | 0.2% | 1.5% | 2.1% | 5.7% | 9.6% |
| | J | 0.1% | 0.3% | 0.4% | 1.1% | 2.4% | 3.4% | 7.6% |
| | Total | 3.8% | 5.0% | 9.2% | 18.0% | 30.2% | 34.0% | 100.0% |

| Compnent | | Clarity | | | | | | | |
|---|---|---|---|---|---|---|---|---|---|
| Range | Color | 1-IF/FL | 2-VVS1 | 3-VVS2 | 4-VS1 | 5-VS2 | 6-SI1 | Total | |
| 1.00-1.19 | | | | | | | | | |
| | | | | | 1 | 1 | | | |
| | | | | 1 | 1 | 2 | 1 | | |
| | | | | | 1 | 2 | 1 | | |
| | | | | | 1 | 1 | 1 | | |
| | Total | | | | | | | 15 | 25% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 1.05 | D | $19,100 | $14,000 | $12,300 | $9,800 | $8,400 | $7,000 |
| | E | $13,400 | $12,500 | $10,700 | $9,200 | $8,000 | $6,600 |
| | F | $12,100 | $11,000 | $10,200 | $8,800 | $7,700 | $6,300 |
| | G | $9,900 | $9,300 | $9,000 | $8,000 | $7,200 | $5,900 |
| | H | $7,900 | $7,600 | $7,200 | $6,600 | $6,200 | $5,700 |
| | I | $6,800 | $6,600 | $6,200 | $5,700 | $5,300 | $5,000 |
| | J | $5,700 | $5,500 | $5,400 | $5,100 | $4,700 | $4,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 1.00-1.19 | D | $0 | $0 | $0 | $0 | $0 | $0 | | | |
| | E | $0 | $0 | $0 | $9,660 | $8,400 | $0 | | | |
| | F | $0 | $0 | $10,710 | $9,240 | $16,170 | $6,615 | | | |
| | G | $0 | $0 | $0 | $8,400 | $15,120 | $6,195 | | | |
| | H | $0 | $0 | $0 | $8,830 | $6,510 | $5,985 | | | |
| | I | $0 | $0 | $0 | $0 | $0 | $5,250 | | | |
| | J | $0 | $0 | $0 | $0 | $0 | $0 | | | |
| | Total | | | | | | | $115,185 | 15.75 | 15 |

FIG. 5
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.20-1.49 | D | 15 | 15 | 27 | 23 | 23 | 30 | 133 |
| | E | 10 | 20 | 26 | 37 | 67 | 57 | 217 |
| | F | 34 | 58 | 86 | 146 | 188 | 99 | 609 |
| | G | 20 | 51 | 92 | 180 | 258 | 137 | 738 |
| | H | 4 | 14 | 40 | 114 | 191 | 233 | 596 |
| | I | 5 | 8 | 13 | 76 | 152 | 154 | 408 |
| | J | 7 | 8 | 7 | 82 | 124 | 116 | 344 |
| | Total | 95 | 172 | 291 | 658 | 1,003 | 826 | 3,045 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 1.20-1.49 | D | 0.5% | 0.5% | 0.9% | 0.8% | 0.8% | 1.0% | 4.4% |
| | E | 0.3% | 0.7% | 0.9% | 1.2% | 2.2% | 1.9% | 7.1% |
| | F | 1.1% | 1.8% | 2.8% | 4.8% | 6.2% | 3.3% | 20.0% |
| | G | 0.7% | 1.7% | 3.0% | 5.9% | 8.5% | 4.5% | 24.2% |
| | H | 0.1% | 0.5% | 1.3% | 3.7% | 6.3% | 7.7% | 19.6% |
| | I | 0.2% | 0.3% | 0.4% | 2.5% | 5.0% | 5.1% | 13.4% |
| | J | 0.2% | 0.3% | 0.2% | 2.7% | 4.1% | 3.6% | 11.3% |
| | Total | 3.1% | 5.6% | 9.6% | 21.6% | 32.9% | 27.1% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.20-1.49 | D | | | | | | | |
| | E | | | | ▨ | | | |
| | F | | ▨ | ▨ | 1 | 1 | ▨ | |
| | G | | | ▨ | 1 | 1 | 1 | |
| | H | | | | 1 | 1 | 1 | |
| | I | | | | ▨ | 1 | 1 | |
| | J | | | | | | | |
| | Total | | | | | | | 9 | 15% |

| $/CT | | Clarity | | | | | |
|---|---|---|---|---|---|---|---|
| | Color | 1-IF/FL | 2-VVS1 | 3-VVS2 | 4-VS1 | 5-VS2 | 6-SI1 |
| 1.27 | D | $20,819 | $15,540 | $13,530 | $11,172 | $9,408 | $7,840 |
| | E | $15,276 | $13,500 | $11,663 | $10,120 | $8,800 | $7,392 |
| | F | $12,826 | $11,980 | $10,710 | $9,592 | $8,470 | $7,056 |
| | G | $10,395 | $9,672 | $9,450 | $8,720 | $7,920 | $6,608 |
| | H | $8,137 | $7,676 | $7,200 | $7,128 | $6,696 | $6,213 |
| | I | $7,616 | $6,666 | $6,572 | $5,985 | $5,777 | $5,450 |
| | J | $5,614 | $5,665 | $5,616 | $5,406 | $5,029 | $4,860 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $0 | $0 | $0 | $0 | | | |
| | F | $0 | $0 | $0 | $12,182 | $10,757 | $0 | | | |
| | G | $0 | $0 | $0 | $11,074 | $10,058 | $8,392 | | | |
| | H | $0 | $0 | $0 | $0 | $8,504 | $7,691 | | | |
| | I | $0 | $0 | $0 | $0 | $7,337 | $6,922 | | | |
| | J | $0 | $0 | $0 | $0 | $0 | $0 | | | |
| | Total | | | | | | | $83,116 | 11.43 | 9 |

FIG. 5
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.50-1.75 | D | 13 | 14 | 24 | 33 | 43 | 50 | 177 |
| | E | 7 | 14 | 30 | 35 | 76 | 95 | 257 |
| | F | 12 | 26 | 54 | 117 | 188 | 142 | 539 |
| | G | 16 | 23 | 56 | 151 | 247 | 161 | 654 |
| | H | 6 | 5 | 16 | 95 | 173 | 204 | 499 |
| | I | 5 | 6 | 23 | 114 | 148 | 175 | 471 |
| | J | 5 | 9 | 31 | 77 | 102 | 78 | 302 |
| | Total | 64 | 97 | 234 | 622 | 977 | 905 | 2,899 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.50-0.59 | D | 0.4% | 0.5% | 0.8% | 1.1% | 1.5% | 1.7% | 6.1% |
| | E | 0.2% | 0.5% | 1.0% | 1.2% | 2.6% | 3.3% | 8.9% |
| | F | 0.4% | 0.9% | 1.9% | 4.0% | 6.5% | 4.9% | 18.6% |
| | G | 0.6% | 0.8% | 1.9% | 5.2% | 8.5% | 5.6% | 22.6% |
| | H | 0.2% | 0.2% | 0.6% | 3.3% | 6.0% | 7.0% | 17.2% |
| | I | 0.2% | 0.2% | 0.8% | 3.9% | 5.1% | 6.0% | 16.2% |
| | J | 0.2% | 0.3% | 1.1% | 2.7% | 3.5% | 2.7% | 10.4% |
| | Total | 2.2% | 3.3% | 8.1% | 21.5% | 33.7% | 31.2% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | | | | | | | | |
| | | | | | | | | |
| | | | | | 1 | 1 | | |
| | | | | | 1 | 1 | 1 | |
| | | | | | 1 | 1 | 1 | |
| | | | | | 1 | 1 | 1 | |
| | | | | | | | | |
| | Total | | | | | | | 9 | 15% |

| $/CT | | Clarity | | | | | |
|---|---|---|---|---|---|---|---|
| | Color | 1-IF/FL | 2-VVS1 | 3-VVS2 | 4-VS1 | 5-VS2 | 6-SI1 |
| 1.58 | D | $22,300 | $17,800 | $16,200 | $13,100 | $11,400 | $9,500 |
| | E | $17,600 | $16,600 | $14,300 | $12,200 | $10,900 | $9,200 |
| | F | $15,700 | $14,100 | $13,400 | $11,700 | $10,400 | $8,700 |
| | G | $12,400 | $11,800 | $11,300 | $10,500 | $9,600 | $7,900 |
| | H | $10,000 | $9,600 | $9,200 | $8,600 | $8,100 | $7,400 |
| | I | $8,500 | $8,300 | $8,000 | $7,700 | $7,000 | $6,500 |
| | J | $7,300 | $7,000 | $6,700 | $6,400 | $5,800 | $5,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $0 | $0 | $0 | $0 | | | |
| | F | $0 | $0 | $0 | $18,466 | $16,432 | $0 | | | |
| | G | $0 | $0 | $0 | $16,590 | $15,166 | $12,482 | | | |
| | H | $0 | $0 | $0 | $0 | $12,798 | $11,692 | | | |
| | I | $0 | $0 | $0 | $0 | $11,060 | $10,270 | | | |
| | J | $0 | $0 | $0 | $0 | $0 | $0 | | | |
| | Total | | | | | | | $124,978 | 14.22 | 9 |

FIG. 5
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 2.00-2.29 | D | 10 | 6 | 16 | 26 | 29 | 23 | 110 |
| | E | 9 | 15 | 12 | 38 | 43 | 35 | 152 |
| | F | 11 | 15 | 17 | 70 | 108 | 81 | 302 |
| | G | 15 | 11 | 23 | 127 | 199 | 144 | 519 |
| | H | 4 | 4 | 9 | 91 | 149 | 142 | 399 |
| | I | 7 | 4 | 16 | 71 | 132 | 146 | 376 |
| | J | 4 | 4 | 12 | 59 | 79 | 99 | 257 |
| | Total | 60 | 59 | 105 | 482 | 739 | 670 | 2115 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 2.00-2.29 | D | 0.5% | 0.3% | 0.8% | 1.2% | 1.4% | 1.1% | 5.2% |
| | E | 0.4% | 0.7% | 0.6% | 1.8% | 2.0% | 1.7% | 7.2% |
| | F | 0.5% | 0.7% | 0.8% | 3.3% | 5.1% | 3.8% | 14.3% |
| | G | 0.7% | 0.5% | 1.1% | 6.0% | 9.4% | 6.8% | 24.5% |
| | H | 0.2% | 0.2% | 0.4% | 4.3% | 7.0% | 6.7% | 18.9% |
| | I | 0.3% | 0.2% | 0.8% | 3.4% | 6.2% | 5.9% | 17.8% |
| | J | 0.2% | 0.2% | 0.6% | 2.8% | 3.7% | 4.7% | 12.2% |
| | Total | 2.8% | 2.8% | 5.0% | 22.8% | 34.9% | 31.7% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | | | | | | | | |
| | | | | | | | | |
| | | | | | | | | |
| | | | | | | | | |
| | | | | | | | | |
| | | | | | | | | |
| | Total | | | | | | | 6 | 10%

| $/CT | | Clarity | | | | | |
|---|---|---|---|---|---|---|---|
| | Color | 1-IF/FL | 2-VVS1 | 3-VVS2 | 4-VS1 | 5-VS2 | 6-SI1 |
| 2.08 | D | $32,600 | $26,100 | $23,700 | $19,600 | $16,000 | $12,600 |
| | E | $25,500 | $23,800 | $20,300 | $17,700 | $15,400 | $12,300 |
| | F | $23,200 | $20,500 | $18,500 | $16,500 | $15,000 | $11,900 |
| | G | $19,000 | $17,400 | $15,800 | $15,200 | $13,900 | $11,200 |
| | H | $14,800 | $13,400 | $12,800 | $12,300 | $11,500 | $10,000 |
| | I | $11,600 | $11,300 | $10,900 | $10,200 | $9,400 | $8,700 |
| | J | $9,500 | $9,100 | $8,900 | $7,600 | $7,000 | $6,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 2.00-2.29 | D | $0 | $0 | $0 | $0 | $0 | $0 | | | |
| | E | $0 | $0 | $0 | $0 | $0 | $0 | | | |
| | F | $0 | $0 | $0 | $0 | $0 | $0 | | | |
| | G | $0 | $0 | $0 | $31,616 | $26,912 | $23,296 | | | |
| | H | $0 | $0 | $0 | $0 | $23,920 | $20,800 | | | |
| | I | $0 | $0 | $0 | $0 | $0 | $18,096 | | | |
| | J | $0 | $0 | $0 | $0 | $0 | $0 | | | |
| | Total | | | | | | | $148,640 | 12.48 | 6 |

FIG. 5
(continued)

|     |       | Clarity |       |       |       |       |       | Total |
|-----|-------|---------|-------|-------|-------|-------|-------|-------|
|     |       | 1-IF/FL | 2-VVS1 | 3-VVS2 | 4-VS1 | 5-VS2 | 6-SI1 |       |
| ALL | D     | -       | -     | -     |       |       |       |       |
|     | E     | -       | -     | 1     | 3     | 2     |       |       |
|     | F     | -       | -     | 2     | 4     | 6     | 2     |       |
|     | G     | -       | -     |       | 7     | 7     | 6     |       |
|     | H     | -       | -     |       | 2     | 5     | 5     |       |
|     | I     | -       | -     |       |       | 3     | 4     |       |
|     | J     | -       | -     |       |       |       |       |       |
|     | Total |         |       |       |       |       |       | 60    | 100%

|     |       | Clarity |        |        |         |         |         | Total  |       |     |
|-----|-------|---------|--------|--------|---------|---------|---------|--------|-------|-----|
|     | Color | 1-IF/FL | 2-VVS1 | 3-VVS2 | 4-VS1   | 5-VS2   | 6-SI1   | Value  | Carat | Qty |
| ALL | D     | $0      | $0     | $0     | $0      | $0      | $0      |        |       |     |
|     | E     | $0      | $0     | $2,703 | $15,862 | $12,100 | $0      |        |       |     |
|     | F     | $0      | $0     | $13,254 | $45,802 | $48,745 | $9,723 |        |       |     |
|     | G     | $0      | $0     | $0     | $75,186 | $74,263 | $54,682 |        |       |     |
|     | H     | $0      | $0     | $0     | $10,038 | $54,692 | $49,032 |        |       |     |
|     | I     | $0      | $0     | $0     | $0      | $21,061 | $40,538 |        |       |     |
|     | J     | $0      | $0     | $0     | $0      | $0      | $0      |        |       |     |
|     | Total |         |        |        |         |         |         |        |       |     |

FIG. 5
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | D | 28 | 60 | 94 | 99 | 75 | 74 | 430 |
| | E | 22 | 58 | 105 | 108 | 94 | 81 | 468 |
| | F | 30 | 39 | 126 | 153 | 146 | 78 | 572 |
| | G | 34 | 67 | 92 | 175 | 145 | 131 | 644 |
| | H | 13 | 23 | 35 | 78 | 88 | 89 | 326 |
| | I | 1 | 10 | 12 | 53 | 84 | 46 | 206 |
| | J | 1 | 7 | 5 | 17 | 48 | 41 | 119 |
| | Total | 129 | 264 | 469 | 683 | 680 | 540 | 2,785 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.50-0.59 | D | 1.0% | 2.2% | 3.4% | 3.6% | 2.7% | 2.7% | 15.6% |
| | E | 0.8% | 2.1% | 3.8% | 3.9% | 3.4% | 2.9% | 16.9% |
| | F | 1.1% | 1.4% | 4.5% | 5.5% | 5.3% | 2.8% | 20.7% |
| | G | 1.2% | 2.4% | 3.3% | 6.3% | 5.2% | 4.7% | 23.3% |
| | H | 0.5% | 0.8% | 1.3% | 2.8% | 3.2% | 3.2% | 11.8% |
| | I | 0.0% | 0.4% | 0.4% | 1.9% | 3.0% | 1.7% | 7.5% |
| | J | 0.0% | 0.3% | 0.3% | 0.6% | 1.7% | 1.5% | 4.3% |
| | Total | 4.7% | 9.5% | 17.0% | 24.7% | 24.6 | 19.5% | 100.0% |

| Component | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | D | | | | | | | |
| | E | | | 1 | 1 | | | |
| | F | | | 1 | 1 | 1 | | |
| | G | | | | 2 | 1 | 1 | |
| | H | | | | | | | |
| | I | | | | | | | |
| | J | | | | | | | |
| | Total | | | | | | | 9 | 15% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 0.53 | D | $7,600 | $6,100 | $5,500 | $4,500 | $4,100 | $3,500 |
| | E | $6,000 | $5,500 | $5,100 | $4,200 | $3,800 | $3,200 |
| | F | $5,500 | $5,100 | $4,800 | $4,000 | $3,600 | $2,900 |
| | G | $5,100 | $4,600 | $4,300 | $3,800 | $3,300 | $2,700 |
| | H | $4,500 | $4,000 | $3,600 | $3,300 | $2,900 | $2,500 |
| | I | $3,700 | $3,300 | $3,000 | $2,700 | $2,500 | $2,200 |
| | J | $2,900 | $2,700 | $2,600 | $2,300 | $2,200 | $2,000 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $2,703 | $2,226 | $0 | $0 | | | |
| | F | $0 | $0 | $2,544 | $2,120 | $1,908 | $0 | | | |
| | G | $0 | $0 | $0 | $4,028 | $1,749 | $1,431 | | | |
| | H | $0 | $0 | $0 | $0 | $0 | $0 | | | |
| | I | $0 | $0 | $0 | $0 | $0 | $0 | | | |
| | J | $0 | $0 | $0 | $0 | $0 | $0 | | | |
| | Total | | | | | | | $18,709 | 4.77 | 9 |

FIG. 6

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.70-0.83 | D | 12 | 14 | 29 | 74 | 90 | 133 | 352 |
| | E | 9 | 41 | 51 | 111 | 182 | 253 | 647 |
| | F | 11 | 53 | 68 | 126 | 185 | 270 | 713 |
| | G | 26 | 50 | 68 | 119 | 185 | 211 | 659 |
| | H | 16 | 41 | 31 | 115 | 134 | 177 | 514 |
| | I | 8 | 39 | 46 | 96 | 159 | 156 | 504 |
| | J | 11 | 9 | 17 | 58 | 74 | 73 | 242 |
| | Total | 93 | 247 | 310 | 699 | 1,009 | 1,273 | 3,631 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.70-0.83 | D | 0.3% | 0.4% | 0.8% | 2.0% | 2.5% | 3.7% | 9.7% |
| | E | 0.2% | 1.1% | 1.4% | 3.15 | 5.0% | 7.0% | 17.8% |
| | F | 0.3% | 1.5% | 1.9% | 3.5% | 5.1% | 7.4% | 19.6% |
| | G | 0.7% | 1.4% | 1.9% | 3.3% | 5.1% | 5.8% | 18.1% |
| | H | 0.4% | 1.1% | 0.9% | 3.2% | 3.7% | 4.9% | 14.2% |
| | I | 0.2% | 1.1% | 1.3% | 2.6% | 4.4% | 4.3% | 13.9% |
| | J | 0.3% | 0.2% | 0.55 | 1.6% | 2.0% | 2.0% | 6.7% |
| | Total | 2.63% | 6.85 | 8.55 | 19.3% | 27.8% | 35.1% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.70-0.83 | | | | | ▨ | ▨ | | |
| | | | | ▨ | ▨ | ▨ | ▨ | |
| | | | | ▨ | ▨ | ▨ | ▨ | |
| | | | | ▨ | ▨ | ▨ | ▨ | |
| | | | | | | | | |
| | Total | | | | | | | 12 | 20% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 0.74 | D | $9,000 | $7,100 | $6,500 | $5,800 | $5,300 | $4,700 |
| | E | $7,000 | $6,600 | $5,900 | $5,400 | $5,000 | $4,500 |
| | F | $6,500 | $6,100 | $5,500 | $5,100 | $4,700 | $4,200 |
| | G | $6,000 | $5,500 | $5,100 | $4,700 | $4,400 | $3,900 |
| | H | $5,400 | $4,900 | $4,500 | $4,200 | $4,000 | $3,600 |
| | I | $4,500 | $4,200 | $4,000 | $3,800 | $3,600 | $3,300 |
| | J | $3,500 | $3,400 | $3,300 | $3,100 | $3,000 | $2,900 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.70-0.83 | D | $0 | $0 | $0 | $0 | $0 | $0 | | | |
| | E | $0 | $0 | $0 | $3,996 | $3,700 | $0 | | | |
| | F | $0 | $0 | $0 | $3,774 | $3,478 | $3,108 | | | |
| | G | $0 | $0 | $0 | $3,478 | $3,256 | $2,886 | | | |
| | H | $0 | $0 | $0 | $3,108 | $2,960 | $2,664 | | | |
| | I | $0 | $0 | $0 | $0 | $2,684 | $0 | | | |
| | J | $0 | $0 | $0 | $0 | $0 | $0 | | | |
| | Total | | | | | | | $39,072 | 8.88 | 12 |

FIG. 6
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.00-1.19 | D | 27 | 17 | 64 | 74 | 78 | 84 | 344 |
| | E | 24 | 47 | 93 | 130 | 185 | 151 | 630 |
| | F | 80 | 106 | 162 | 213 | 368 | 231 | 1,160 |
| | G | 41 | 53 | 97 | 243 | 424 | 363 | 1,221 |
| | H | 14 | 9 | 15 | 116 | 328 | 429 | 821 |
| | I | 1 | 6 | 11 | 74 | 108 | 286 | 486 |
| | J | 4 | 13 | 20 | 56 | 121 | 170 | 384 |
| | Total | 191 | 251 | 462 | 906 | 1,522 | 1,714 | 5,046 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 1.00-1.19 | D | 0.5% | 0.3% | 1.3% | 1.5% | 1.5% | 1.7% | 6.8% |
| | E | 0.5% | 0.9% | 1.8% | 2.8% | 3.7% | 3.0% | 12.5% |
| | F | 1.6% | 2.1% | 3.2% | 4.2% | 7.3% | 4.6% | 23.0% |
| | G | 0.8% | 1.1% | 1.9% | 4.6% | 8.4% | 7.2% | 24.2% |
| | H | 0.3% | 0.2% | 0.3% | 2.3% | 4.7% | 8.5% | 16.3% |
| | I | 0.0% | 0.1% | 0.2% | 1.5% | 2.1% | 5.7% | 9.6% |
| | J | 0.1% | 0.3% | 0.4% | 1.1% | 2.4% | 3.4% | 7.6% |
| | Total | 3.8% | 5.0% | 9.2% | 18.0% | 30.2% | 34.0% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.00-1.19 | | | | | 1 | 1 | | |
| | | | | 1 | 1 | 2 | 1 | |
| | | | | | 1 | 2 | 1 | |
| | | | | | 1 | 1 | 1 | |
| | Total | | | | | | | 15 | 25% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 1.05 | D | $19,100 | $14,000 | $12,300 | $9,800 | $8,400 | $7,000 |
| | E | $13,400 | $12,500 | $10,700 | $9,200 | $8,000 | $6,600 |
| | F | $12,100 | $11,000 | $10,200 | $8,800 | $7,700 | $6,300 |
| | G | $9,900 | $9,300 | $9,000 | $8,000 | $7,200 | $5,900 |
| | H | $7,900 | $7,600 | $7,200 | $6,600 | $6,200 | $5,700 |
| | I | $6,800 | $6,600 | $6,200 | $5,700 | $5,300 | $5,000 |
| | J | $5,700 | $5,500 | $5,400 | $5,100 | $4,700 | $4,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 1.00-1.19 | D | $0 | $0 | $0 | $0 | $0 | $0 | | | |
| | E | $0 | $0 | $0 | $9,660 | $8,400 | $0 | | | |
| | F | $0 | $0 | $10,710 | $9,240 | $16,170 | $6,615 | | | |
| | G | $0 | $0 | $0 | $8,400 | $15,120 | $6,195 | | | |
| | H | $0 | $0 | $0 | $8,830 | $6,510 | $5,985 | | | |
| | I | $0 | $0 | $0 | $0 | $0 | $5,250 | | | |
| | J | $0 | $0 | $0 | $0 | $0 | $0 | | | |
| | Total | | | | | | | $115,185 | 15.75 | 15 |

FIG. 6
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.20-1.49 | D | 15 | 15 | 27 | 23 | 23 | 30 | 133 |
| | E | 10 | 20 | 26 | 37 | 67 | 57 | 217 |
| | F | 34 | 58 | 86 | 146 | 188 | 99 | 609 |
| | G | 20 | 51 | 92 | 180 | 258 | 137 | 738 |
| | H | 4 | 14 | 40 | 114 | 191 | 233 | 596 |
| | I | 5 | 8 | 13 | 76 | 152 | 154 | 408 |
| | J | 7 | 8 | 7 | 82 | 124 | 116 | 344 |
| | Total | 95 | 172 | 291 | 658 | 1,003 | 826 | 3,045 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 1.20-1.49 | D | 0.5% | 0.5% | 0.9% | 0.8% | 0.8% | 1.0% | 4.4% |
| | E | 0.3% | 0.7% | 0.9% | 1.2% | 2.2% | 1.9% | 7.1% |
| | F | 1.1% | 1.8% | 2.8% | 4.8% | 6.2% | 3.3% | 20.0% |
| | G | 0.7% | 1.7% | 3.0% | 5.9% | 8.5% | 4.5% | 24.2% |
| | H | 0.1% | 0.5% | 1.3% | 3.7% | 6.3% | 7.7% | 19.6% |
| | I | 0.2% | 0.3% | 0.4% | 2.5% | 5.0% | 5.1% | 13.4% |
| | J | 0.2% | 0.3% | 0.2% | 2.7% | 4.1% | 3.6% | 11.3% |
| | Total | 3.1% | 5.6% | 9.6% | 21.6% | 32.9% | 27.1% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.20-1.49 | D | | | | | | | |
| | E | | | | ▨ | | | |
| | F | | ▨ | ▨ | ▨ | ▨ | ▨ | |
| | G | | | ▨ | ▨ | ▨ | ▨ | |
| | H | | | | ▨ | ▨ | ▨ | |
| | I | | | | ▨ | ▨ | ▨ | |
| | J | | | | | | | |
| | Total | | | | | | | 9 | 15%

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 1.27 | D | $20,819 | $15,540 | $13,530 | $11,172 | $9,408 | $7,840 |
| | E | $15,276 | $13,500 | $11,663 | $10,120 | $8,800 | $7,392 |
| | F | $12,826 | $11,980 | $10,710 | $9,592 | $8,470 | $7,056 |
| | G | $10,395 | $9,672 | $9,450 | $8,720 | $7,920 | $6,608 |
| | H | $8,137 | $7,676 | $7,200 | $7,128 | $6,696 | $6,213 |
| | I | $7,616 | $6,666 | $6,572 | $5,985 | $5,777 | $5,450 |
| | J | $5,614 | $5,665 | $5,616 | $5,406 | $5,029 | $4,860 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $0 | $0 | $0 | $0 | | | |
| | F | $0 | $0 | $0 | $12,182 | $10,757 | $0 | | | |
| | G | $0 | $0 | $0 | $11,074 | $10,058 | $8,392 | | | |
| | H | $0 | $0 | $0 | $0 | $8,504 | $7,691 | | | |
| | I | $0 | $0 | $0 | $0 | $7,337 | $6,922 | | | |
| | J | $0 | $0 | $0 | $0 | $0 | $0 | | | |
| | Total | | | | | | | $83,116 | 11.43 | 9 |

FIG. 6
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 1.50-1.75 | D | 13 | 14 | 24 | 33 | 43 | 50 | 177 |
| | E | 7 | 14 | 30 | 35 | 76 | 95 | 257 |
| | F | 12 | 26 | 54 | 117 | 188 | 142 | 539 |
| | G | 16 | 23 | 56 | 151 | 247 | 161 | 654 |
| | H | 6 | 5 | 16 | 95 | 173 | 204 | 499 |
| | I | 5 | 6 | 23 | 114 | 148 | 175 | 471 |
| | J | 5 | 9 | 31 | 77 | 102 | 78 | 302 |
| | Total | 64 | 97 | 234 | 622 | 977 | 905 | 2,899 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 0.50-0.59 | D | 0.4% | 0.5% | 0.8% | 1.1% | 1.5% | 1.7% | 6.1% |
| | E | 0.2% | 0.5% | 1.0% | 1.2% | 2.6% | 3.3% | 8.9% |
| | F | 0.4% | 0.9% | 1.9% | 4.0% | 6.5% | 4.9% | 18.6% |
| | G | 0.6% | 0.8% | 1.9% | 5.2% | 8.5% | 5.6% | 22.6% |
| | H | 0.2% | 0.2% | 0.6% | 3.3% | 6.0% | 7.0% | 17.2% |
| | I | 0.2% | 0.2% | 0.8% | 3.9% | 5.1% | 6.0% | 16.2% |
| | J | 0.2% | 0.3% | 1.1% | 2.7% | 3.5% | 2.7% | 10.4% |
| | Total | 2.2% | 3.3% | 8.1% | 21.5% | 33.7% | 31.2% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | | | | | | | | |
| | | | | | | | | |
| | | | | | ░ | ░ | | |
| | | | | ░ | 1 | 1 | ░ | |
| | | | | ░ | 1 | 1 | ░ | |
| | | | | | 1 | 1 | | |
| | | | | | 1 | 1 | | |
| | | | | | ░ | ░ | | |
| | Total | | | | | | | 9 |

15%

| $/CT | | Clarity | | | | | |
|---|---|---|---|---|---|---|---|
| | Color | 1-IF/FL | 2-VVS1 | 3-VVS2 | 4-VS1 | 5-VS2 | 6-SI1 |
| 1.58 | D | $22,300 | $17,800 | $16,200 | $13,100 | $11,400 | $9,500 |
| | E | $17,600 | $16,600 | $14,300 | $12,200 | $10,900 | $9,200 |
| | F | $15,700 | $14,100 | $13,400 | $11,700 | $10,400 | $8,700 |
| | G | $12,400 | $11,800 | $11,300 | $10,500 | $9,600 | $7,900 |
| | H | $10,000 | $9,600 | $9,200 | $8,600 | $8,100 | $7,400 |
| | I | $8,500 | $8,300 | $8,000 | $7,700 | $7,000 | $6,500 |
| | J | $7,300 | $7,000 | $6,700 | $6,400 | $5,800 | $5,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 0.50-0.59 | D | $0 | $0 | $0 | $0 | $0 | $0 | | | |
| | E | $0 | $0 | $0 | $0 | $0 | $0 | | | |
| | F | $0 | $0 | $0 | $18,466 | $16,432 | $0 | | | |
| | G | $0 | $0 | $0 | $16,590 | $15,166 | $12,482 | | | |
| | H | $0 | $0 | $0 | $0 | $12,798 | $11,692 | | | |
| | I | $0 | $0 | $0 | $0 | $11,060 | $10,270 | | | |
| | J | $0 | $0 | $0 | $0 | $0 | $0 | | | |
| | Total | | | | | | | $124,978 | 14.22 | 9 |

FIG. 6
(continued)

| Count | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 2.00-2.29 | D | 10 | 6 | 16 | 26 | 29 | 23 | 110 |
| | E | 9 | 15 | 12 | 38 | 43 | 35 | 152 |
| | F | 11 | 15 | 17 | 70 | 108 | 81 | 302 |
| | G | 15 | 11 | 23 | 127 | 199 | 144 | 519 |
| | H | 4 | 4 | 9 | 91 | 149 | 142 | 399 |
| | I | 7 | 4 | 16 | 71 | 132 | 146 | 376 |
| | J | 4 | 4 | 12 | 59 | 79 | 99 | 257 |
| | Total | 60 | 59 | 105 | 482 | 739 | 670 | 2115 |

| %Total | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | %Total |
| 2.00-2.29 | D | 0.5% | 0.3% | 0.8% | 1.2% | 1.4% | 1.1% | 5.2% |
| | E | 0.4% | 0.7% | 0.6% | 1.8% | 2.0% | 1.7% | 7.2% |
| | F | 0.5% | 0.7% | 0.8% | 3.3% | 5.1% | 3.8% | 14.3% |
| | G | 0.7% | 0.5% | 1.1% | 6.0% | 9.4% | 6.8% | 24.5% |
| | H | 0.2% | 0.2% | 0.4% | 4.3% | 7.0% | 6.7% | 18.9% |
| | I | 0.3% | 0.2% | 0.8% | 3.4% | 6.2% | 5.9% | 17.8% |
| | J | 0.2% | 0.2% | 0.6% | 2.8% | 3.7% | 4.7% | 12.2% |
| | Total | 2.8% | 2.8% | 5.0% | 22.8% | 34.9% | 31.7% | 100.0% |

| Compnent | | Clarity | | | | | | |
|---|---|---|---|---|---|---|---|---|
| Range | Color | 1-IF/FL | 2-VVS1 | 3-VVS2 | 4-VS1 | 5-VS2 | 6-SI1 | Total |
| 0.50-0.59 | | | | | | | | |
| | | | | | | | | |
| | | | | | | | | |
| | | | | | | | | |
| | | | | | | | | |
| | | | | | | | | |
| | | | | | | | | |
| | Total | | | | | | | 6 | 10% |

| $/CT | Color | Clarity | | | | | |
|---|---|---|---|---|---|---|---|
| | | 1-IF/FL | 2-VVS1 | 3-VVS2 | 4-VS1 | 5-VS2 | 6-SI1 |
| 2.08 | D | $32,600 | $26,100 | $23,700 | $19,600 | $16,000 | $12,600 |
| | E | $25,500 | $23,800 | $20,300 | $17,700 | $15,400 | $12,300 |
| | F | $23,200 | $20,500 | $18,500 | $16,500 | $15,000 | $11,900 |
| | G | $19,000 | $17,400 | $15,800 | $15,200 | $13,900 | $11,200 |
| | H | $14,800 | $13,400 | $12,800 | $12,300 | $11,500 | $10,000 |
| | I | $11,600 | $11,300 | $10,900 | $10,200 | $9,400 | $8,700 |
| | J | $9,500 | $9,100 | $8,900 | $7,600 | $7,000 | $6,500 |
| | Total | | | | | | |

| Value Cal. | | Clarity | | | | | | Total | | |
|---|---|---|---|---|---|---|---|---|---|---|
| Range | Color | 1-IF/FL | 2-VVS1 | 3-VVS2 | 4-VS1 | 5-VS2 | 6-SI1 | Value | Carat | Qty |
| 2.00-2.29 | D | $0 | $0 | $0 | $0 | $0 | $0 | | | |
| | E | $0 | $0 | $0 | $0 | $0 | $0 | | | |
| | F | $0 | $0 | $0 | $0 | $0 | $0 | | | |
| | G | $0 | $0 | $0 | $31,616 | $26,912 | $23,296 | | | |
| | H | $0 | $0 | $0 | $0 | $23,920 | $20,800 | | | |
| | I | $0 | $0 | $0 | $0 | $0 | $18,096 | | | |
| | J | $0 | $0 | $0 | $0 | $0 | $0 | | | |
| | Total | | | | | | | $148,640 | 12.48 | 6 |

FIG. 6
(continued)

|  |  | Clarity | | | | | | Total |
|---|---|---|---|---|---|---|---|---|
|  |  | 1-IF/FL | 2-VVS1 | 3-VVS2 | 4-VS1 | 5-VS2 | 6-SI1 |  |
| ALL | D | - | - | - |  |  |  |  |
|  | E | - | - | 1 | 3 | 2 |  |  |
|  | F | - | - | 2 | 4 | 6 | 2 |  |
|  | G | - | - |  | 7 | 7 | 6 |  |
|  | H | - | - |  | 2 | 5 | 5 |  |
|  | I | - | - |  |  | 3 | 4 |  |
|  | J | - | - |  |  |  |  |  |
|  | Total |  |  |  |  |  |  | 60 | 100% |

|  |  | Clarity | | | | | | Total | | |
|---|---|---|---|---|---|---|---|---|---|---|
|  | Color | 1-IF/FL | 2-VVS1 | 3-VVS2 | 4-VS1 | 5-VS2 | 6-SI1 | Value | Carat | Qty |
| ALL | D | $0 | $0 | $0 | $0 | $0 | $0 |  |  |  |
|  | E | $0 | $0 | $2,703 | $15,862 | $12,100 | $0 |  |  |  |
|  | F | $0 | $0 | $13,254 | $45,802 | $48,745 | $9,723 |  |  |  |
|  | G | $0 | $0 | $0 | $75,186 | $74,263 | $54,682 |  |  |  |
|  | H | $0 | $0 | $0 | $10,038 | $54,692 | $49,032 |  |  |  |
|  | I | $0 | $0 | $0 | $0 | $21,061 | $40,538 |  |  |  |
|  | J | $0 | $0 | $0 | $0 | $0 | $0 |  |  |  |
|  | Total |  |  |  |  |  |  |  |  |  |

FIG. 6
(continued)

| Weight Class I | | Clarity | | | | | |
|---|---|---|---|---|---|---|---|
| 0.50-0.59 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class I | Min. Qty | Min. Wt. | Value |
|---|---|---|---|
| Bundle A | 1 | 0.50 | 1,900 |
| Bundle B | 1 | 0.50 | 1,650 |
| Bundle C | 1 | 0.50 | 1,450 |
| Class Total | 3 | 1.5 | 5,000 |

| Weight Class II | | Clarity | | | | | |
|---|---|---|---|---|---|---|---|
| 0.70-0.83 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class II | Min. Qty | Min. Wt. | Value |
|---|---|---|---|
| Bundle A | 1 | 0.70 | 3,490 |
| Bundle B | 2 | 1.40 | 5,600 |
| Bundle C | 1 | 0.70 | 2,320 |
| Class Total | 4 | 2.80 | 11,410 |

| Weight Class III | | Clarity | | | | | |
|---|---|---|---|---|---|---|---|
| 1.00-1.19 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class III | Min. Qty | Min. Wt. | Value |
|---|---|---|---|
| Bundle A | 1 | 1.00 | 8,300 |
| Bundle B | 1 | 1.00 | 6,400 |
| Bundle C | 1 | 1.00 | 5,900 |
| Bundle D | 2 | 2.00 | 14,800 |
| Class Total | 5 | 5.00 | 35,400 |

Note: *** indicates higher carat weight can be used to balance value

\* Value is based on the current diamond wholesale trading system

FIG. 8A

| Weight Class IV | | Clarity | | | | | |
|---|---|---|---|---|---|---|---|
| 1.20-1.49 | Color | 1-IF/FL | 2-VVS1 | 3-VVS2 | 4-VS1 | 5-VS2 | 6-SI1 |
| | D | | | | | | |
| | E | | | | 1b | | |
| | F | | | | | | |
| | G | | | | 1a | | |
| | H | | | | | | |
| | I | | | | | | |
| | J | | | | | | |

| Weight Class IV | Min. Qty | Min. Wt. | Value |
|---|---|---|---|
| Bundle A | 1 | 1.20 | 9,300 |
| Bundle B | 1 | 1.20 | 7,660 |
| Bundle C | 1 | 1.20 | 9,560 |
| Bundle D | 0 | 0 | 0 |
| Class Total | 3 | 3.60 | 26,520 |

| Weight Class V | | Clarity | | | | | |
|---|---|---|---|---|---|---|---|
| 1.50-1.75 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class V | Min. Qty | Min. Wt. | Value |
|---|---|---|---|
| Bundle A | 1 | 1.50 | 10,100 |
| Bundle B | 1 | 1.50 | 15,900 |
| Bundle C | 1 | 1.50 | 19,200 |
| Class Total | 3 | 4.50 | 45,300 |

| Weight Class VI | | Clarity | | | | | |
|---|---|---|---|---|---|---|---|
| 2.00-2.39 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class VI | Min. Qty | Min. Wt. | Value |
|---|---|---|---|
| Bundle A | 0 | 0.00 | 0 |
| Bundle B | 2 | 4.00 | 50,800 |
| Bundle C | 0 | 0.00 | 0 |
| Class Total | 2 | 4.00 | 50,800 |

Note: *** indicates higher carat weight can be used to balance value

| | Min. Qty | Min. Wt. | Value* |
|---|---|---|---|
| Grand Total | 20 | 21.40 | 174,430 |

* Value is based on the current diamond wholesale trading system

FIG. 8A
(continued)

| Weight Class I | | Clarity | | | | | |
|---|---|---|---|---|---|---|---|
| 0.50-0.59 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class I | Min. Qty | Min. Wt. | Value |
|---|---|---|---|
| Bundle A | 1 | 0.51 | 1,938 |
| Bundle B | 1 | 0.52 | 1,716 |
| Bundle C | 1 | 0.50 | 1,450 |
| Class Total | 3 | 1.53 | 5,104 |

| Weight Class II | | Clarity | | | | | |
|---|---|---|---|---|---|---|---|
| 0.70-0.83 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class II | Min. Qty | Min. Wt. | Value |
|---|---|---|---|
| Bundle A | 1 | 0.70 | 3,290 |
| Bundle B | 2 | 1.42 | 5,964 |
| Bundle C | 1 | 0.71 | 2,556 |
| Class Total | 4 | 2.83 | 11,810 |

| Weight Class III | | Clarity | | | | | |
|---|---|---|---|---|---|---|---|
| 1.00-1.19 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class III | Min. Qty | Min. Wt. | Value |
|---|---|---|---|
| Bundle A | 1 | 1.06 | 9,374 |
| Bundle B | 1 | 1.00 | 6,400 |
| Bundle C | 1 | 1.01 | 5,559 |
| Bundle D | 2 | 2.01 | 15,377 |
| Class Total | 5 | 5.00 | 36,110 |

Note: *** indicates higher carat weight can be used to balance value

\* Value is based on the current diamond wholesale trading system

FIG. 8B

| Weight Class IV | | Clarity | | | | | |
|---|---|---|---|---|---|---|---|
| 1.20-1.49 | Color | 1-IF/FL | 2-WS1 | 3-WS2 | 4-VS1 | 5-VS2 | 6-SI1 |
| | D | | | | | 1 | |
| | E | | | | 1 | | |
| | F | | | | | | |
| | G | | | | | | |
| | H | | | | | | |
| | I | | | | | 1 | |
| | J | | | | | | |

| Weight Class IV | Min. Qty | Min. Wt. | Value |
|---|---|---|---|
| Bundle A | 0 | 0 | 0 |
| Bundle B | 0 | 0 | 0 |
| Bundle C | 2 | 2.52 | 19,278 |
| Bundle D | 1 | 1.24 | 7,316 |
| Class Total | 3 | 3.76 | 26,594 |

| Weight Class V | | Clarity | | | | | |
|---|---|---|---|---|---|---|---|
| 1.50-1.75 | Color | 1-IF/FL | 2-WS1 | 3-WS2 | 4-VS1 | 5-VS2 | 6-SI1 |
| | D | | | | | | 1 |
| | E | | | | | | |
| | F | | | | | | |
| | G | | 1 | | | | |
| | H | | | | | | |
| | I | | | | | 1 | |
| | J | | | | | | |

| Weight Class V | Min. Qty | Min. Wt. | Value |
|---|---|---|---|
| Bundle A | 1 | 1.56 | 11,232 |
| Bundle B | 1 | 1.60 | 15,200 |
| Bundle C | 1 | 1.54 | 18,942 |
| Class Total | 3 | 4.70 | 45,374 |

| Weight Class VI | | Clarity | | | | | |
|---|---|---|---|---|---|---|---|
| 2.00-2.39 | Color | 1-IF/FL | 2-WS1 | 3-WS2 | 4-VS1 | 5-VS2 | 6-SI1 |
| | D | | | | | | |
| | E | | | | | | |
| | F | | | | | | |
| | G | | | | | 1 | |
| | H | | | | | | |
| | I | | | | 1 | | |
| | J | | | | | | |

| Weight Class VI | Min. Qty | Min. Wt. | Value |
|---|---|---|---|
| Bundle A | 1 | 2.06 | 21,630 |
| Bundle B | 0 | 0.00 | 0 |
| Bundle C | 1 | 2.04 | 29,172 |
| Class Total | 2 | 4.10 | 50,802 |

| | Min. Qty | Min. Wt. | Value* |
|---|---|---|---|
| Grand Total | 20 | 21.86 | 174,506 |

* Value is based on the current diamond wholesale trading system

Note: *** indicates higher carat weight can be used to balance value

FIG. 8B
(continued)

| Weight Class I | | Clarity | | | | | |
|---|---|---|---|---|---|---|---|
| 0.50-0.59 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class I | Min. Qty | Min. Wt. | Value |
|---|---|---|---|
| Bundle A | 1 | 0.50 | 1,000 |
| Bundle B | 1 | 0.51 | 1,883 |
| Bundle C | 1 | 0.50 | 1,800 |
| Class Total | 3 | 1.51 | 5,283 |

| Weight Class II | | Clarity | | | | | |
|---|---|---|---|---|---|---|---|
| 0.70-0.83 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | 3,500 | 3,400 | 3,300 | 3,100 | 3,000 | 2,900 |

| Weight Class II | Min. Qty | Min. Wt. | Value |
|---|---|---|---|
| Bundle A | 1 | 0.71 | 3,137 |
| Bundle B | 2 | 1.41 | 6,134 |
| Bundle C | 1 | 0.70 | 2,000 |
| Class Total | 4 | 2.82 | 12,131 |

| Weight Class III | | Clarity | | | | | |
|---|---|---|---|---|---|---|---|
| 1.00-1.19 | Color | 1-IF/FL | 2-VVS1 | 3-VVS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class III | Min. Qty | Min. Wt. | Value |
|---|---|---|---|
| Bundle A | 1 | 1.00 | 8,100 |
| Bundle B | 1 | 1.01 | 8,363 |
| Bundle C | 1 | 1.06 | 5,042 |
| Bundle D | 2 | 2.00 | 15,800 |
| Class Total | 5 | 5.07 | 36,305 |

Note: *** indicates higher carat weight can be used to balance value

* Value is based on the current diamond wholesale trading system

FIG. 8C

| Weight Class IV | | Clarity | | | | | |
|---|---|---|---|---|---|---|---|
| 1.20-1.49 | Color | 1-IF/FL | 2-WS1 | 3-WS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class IV | Min. Qty | Min. Wt. | Value |
|---|---|---|---|
| Bundle A | 1 | 1.27 | 10,130 |
| Bundle B | 1 | 1.22 | 7,589 |
| Bundle C | 1 | 1.20 | 9,000 |
| Bundle D | | | |
| Class Total | 3 | 3.69 | 26,719 |

| Weight Class V | | Clarity | | | | | |
|---|---|---|---|---|---|---|---|
| 1.50-1.75 | Color | 1-IF/FL | 2-WS1 | 3-WS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class V | Min. Qty | Min. Wt. | Value |
|---|---|---|---|
| Bundle A | 1 | 1.51 | 11,108 |
| Bundle B | 1 | 1.73 | 15,051 |
| Bundle C | 1 | 1.60 | 19,200 |
| Class Total | 3 | 4.94 | 45,360 |

| Weight Class VI | | Clarity | | | | | |
|---|---|---|---|---|---|---|---|
| 2.00-2.39 | Color | 1-IF/FL | 2-WS1 | 3-WS2 | 4-VS1 | 5-VS2 | 6-SI1 |
| | D | | | | | | |
| | E | | | | | | |
| | F | | | | | | |
| | G | | | | | | |
| | H | | | | | | |
| | I | | | | | | |
| | J | | | | | | |

| Weight Class VI | Min. Qty | Min. Wt. | Value |
|---|---|---|---|
| Bundle A | 1 | 2.01 | 20,100 |
| Bundle B | 0 | 0.00 | 0 |
| Bundle C | 1 | 2.00 | 31,400 |
| Class Total | 2 | 4.01 | 51,500 |

| | Min. Qty | Min. Wt. | Value* |
|---|---|---|---|
| Grand Total | 20 | 21.86 | 174,506 |

\* Value is based on the current diamond wholesale trading system

Note: \*\*\* indicates higher carat weight can be used to balance value

FIG. 8C
(continued)

GLOBAL INVESTMENT GRADE FOR NATURAL AND SYNTHETIC GEMS USED IN FINANCIAL INVESTMENTS AND COMMERCIAL TRADING AND METHOD OF CREATING STANDARDIZED BASKETS OF GEMS TO BE USED IN FINANCIAL AND COMMERCIAL PRODUCTS

This application claims the benefit of U.S. Provisional Application No. 61/972,326, filed Mar. 27, 2008 and U.S. Provisional Application No. 61/089,204, filed Aug. 15, 2008.

The invention relates in general to a method of standardization of natural or synthetic gems (diamonds, rubies, sapphires and emeralds) in order to enable the delivery of a standardized, fungible and certified global investment grade gem to be used in financial and commercial products. The invention also relates to a standardized basket of gems created using the inventive method. The standardized basket of gems may be used in financial products such as futures contracts, options, exchange-traded funds or any other regulated or unregulated financial vehicle.

The invention also relates to an exchange-traded fund comprising a collection of any number of precious gems (diamonds, rubies, sapphires and emeralds), wherein the gems are stored with one or more custodians in exchange for one or more creation units; wherein each creation unit represents a plurality of shares of the fund; and wherein each creation unit is redeemable for an amount of the collection equal to the net asset value of the creation unit plus interest and less fund expenses. Also disclosed is a closed end fund comprising: one or more gem collection instruments; and the distribution of shares of the fund to one or more investors, wherein the shares of the fund have a net asset value based on a combination of prices of the one or more gem collections from a plurality of sources and a cash component or other store of value, and wherein interest earned on the short-term interest bearing instrument of the cash component less expenses are paid out to the one or more investors as a dividend.

The invention also includes using future contracts based on the standardized basket of gems as the deliverable.

The invention also includes a method for converting gems including diamonds to shares of a fund tradable on a secondary market. The secondary market may be regulated or unregulated, over the counter or any other venue that brings buyers and sellers together to trade for example futures, options, equities, or any other financial instrument.

The invention also includes a standard for investment grade gems and the method of generating the standard. The invention also includes an investment grade diamond index and on investment grade diamond benchmark that may be used with financial instruments.

One aspect of the invention is directed to a standardized basket of gems such as diamonds, rubies, sapphires and emeralds, but will described below in detail using diamonds as the exemplar. It should be understood that the invention described herein is also applicable to a standardized basket of any combination of diamonds, rubies, sapphires and emeralds.

BACKGROUND OF THE INVENTION

Diamonds represent an important commodity with an annual world production value of approximately $13 billion with another $63 billion in annual global sales of diamond jewelry. Roughly 49% of diamonds originate in central and southern Africa with significant sources discovered in Canada, India, Russia, Brazil and Australia. Historically, the De Beers Group has held the distinction of the world's largest diamond miner. De Beers maintains an estimated 35-45% market share but their dominance is muted in recent years resulting in increasing competition. Some 80% of rough diamonds pass through Antwerp while approximately 80% of the finished products are sold in the U.S. Some 26 registered diamond bourses comprise the World Federation of Diamond Bourses where wholesalers and retailers may buy gems and subsequently prepare them for final retail sale. Diamond prices vary as a function of the gem's weight (measured in carats), color, clarity, cut and shape among others, as well as dynamic market factors. They are assayed and valued largely by automated, rather than manual, methods. The Gemological Institute of America (GIA) is a recognized organization that grades diamonds. But there is no structured derivatives market either on an over-the-counter (OTC) or exchange-traded basis for diamonds today.

In the past, products such as oil, gold, and corn, have been commoditized and standardized for trading. Diamonds have not, primarily for the reason that many would argue that each diamond is unique and impossible to commoditize because it has been observed that diamonds with identical gemological characteristics look entirely different from each other. Some of these diamonds with identical gemological characteristics look more spectacular than others due to the way that these diamonds are cut (cut quality). These visual differences typically fuel the argument that diamonds cannot be standardized because of pricing discrepancies between gemologically identical diamonds with visible visual differences.

One aspect of the present invention combines gemological and objective analysis of the diamonds, particularly with respect to light and optical behavior, and thereby eliminates these visual discrepancies and produces a fungible standard for classifying diamonds that can be used to securitize or commoditize diamonds. Diamonds bundled under the present invention would not only be gemologically identical, but also exhibit substantially identical optical characteristics such that they would be visually indistinguishable by anyone. Thus, consistent pricing considerations for fungibility can be utilized. Alternatively, the invention can also be used to bundle gemologically dissimilar diamonds with substantially similar monetary values to create standardized fungible baskets. In another alternative, the invention is directed to a basket and method of creating a basket of different gems (i.e., a combination of any of 1 or more collections of diamonds, rubies, sapphires and emeralds) with each created basket having a substantially equivalent monetary value.

In brief, one embodiment of the invention would be a method for standardizing a collection of diamonds. Another embodiment of the invention includes a method of trading a commoditized basket of diamonds. Yet another embodiment of the invention is simply a basket of fungible commoditized diamonds. Still another embodiment of the invention is an Exchange Traded Fund ("ETF") comprised of a standardized basket of diamonds and a cash component. Still another embodiment of the invention are future contracts, equity products, options and other derivative products based on standardized basket of diamonds created under the present invention.

BRIEF DESCRIPTION OF THE SEVERAL VIEWS OF THE DRAWINGS

FIG. 5 is a chart illustrating groupings of commercially available diamonds selected using the claimed invention;

FIG. 6 is a sampling of commercially available diamonds that meet the gemological standards and the objective optical standards of the present invention;

FIG. 8A-C are a series of charts illustrating the numerous requirements for the Value Equivalent Bundling Concept in accordance with the present invention.

DETAILED DESCRIPTION OF THE INVENTION

In accordance with the present invention, a preferred exemplary embodiment of the method for creating a standardized basket of diamonds is described below. Although the preferred embodiment is directed to diamonds, the invention is not limited to diamonds, but should be understood to include all precious gems including rubies, sapphires, emeralds as well as synthetic diamonds. The standardized gem diamond collection of the present invention which may be used in any financial instrument is created using gemological and optical standards as well as market factors to identify appropriate diamonds for inclusion in the standardized basket in the following manner. It should be understood that variations in the creation of the standardized basket may be used, such as for example, the size of the diamonds, the number of the diamonds, and the value of comparable diamonds may be adjusted and still fall within the spirit and scope of the invention.

Initially, the diamonds (or other gems) selected for use in a standardized collection must meet a minimum gemological standard. The gemological standard would require that every single diamond that can be included in the standardized collection must eventually conform to the following gemological identification requirements:

All natural polished diamonds must be evaluated and identified by its gemological classifications. These include:
1. Color,
2. Clarity (including a plot plan of its inclusion and natural characteristics),
3. Carat weight,
4. Shape,
5. Cut Grade,
6. Measurements,
7. General proportions,
8. Finish,
9. Fluorescence,
10. Surface Characteristics,
11. Culet.

Figure 1:
FIG. 1 is an example of a GIA Diamond Grading Report.

These characteristics will be classified using GIA Diamond Grading Reports of the Gemological Institute of America. All fundamental gemological information known as the 4' C's (color, clarity, carat weight, cut) should be provided by a GIA Diamond Grading Report. An example of a report is shown in FIG. 1. GIA grading standards are well known in the industry and are the preferred gemological grading standards for the present invention. However, other recognized gemological grading standards may also be used so long as the characteristics are substantially similar to the standards used by the GIA or can be correlated thereto. Gemological grading standards for other types of gems such as rubies, sapphires and emeralds may also be used.

Gemological Requirements for diamonds that will be part of the standardized basket of diamonds and may be used in financial instruments must meet the following requirements:

Color: The diamonds must meet the GIA standards of or equivalent to D to J.

Clarity: The diamonds must meet the GIA standards of or equivalent to IF to SII. Absolutely no milky or cloudy material should be present. "Clarity based on cloud that are not shown" types are not acceptable for trading. In addition, no weak or borderline ratings are acceptable.

Carat weight: Preferred ranges will be limited to 0.50 to 2.20 carats. It is, however, within the spirit of the invention to use different ranges of diamond sizes to create a basket so long as the range is consistent. These would include for example, very large stones (i.e., greater than 3 carats), very small stones (less than 0.25 carats), as well as rough stones.

Shape: The diamonds should be generic round brilliant cut with 57 to 58 facets.

Cut Grade The cut should meet the GIA "Excellent" rating, but may include a "Very Good" rating as well.

Measurements: All measurements should be made in millimeter scale.

General proportions: The general proportions of the diamond must be in the "Excellent" range.

Finish Polish The diamond must meet an "Excellent" to "Very Good" rating.

Symmetry: The diamond must meet an "Excellent" to "Very Good" rating.

Fluorescence: The diamond must be graded showing none or faint, but in some instances may possibly include medium blue.

Surface Characteristics: The diamonds must not have any natural unfinished surfaces, no excessive graining and no extra facets.

Culet: Must be rated as none to very small.

Figure 2:
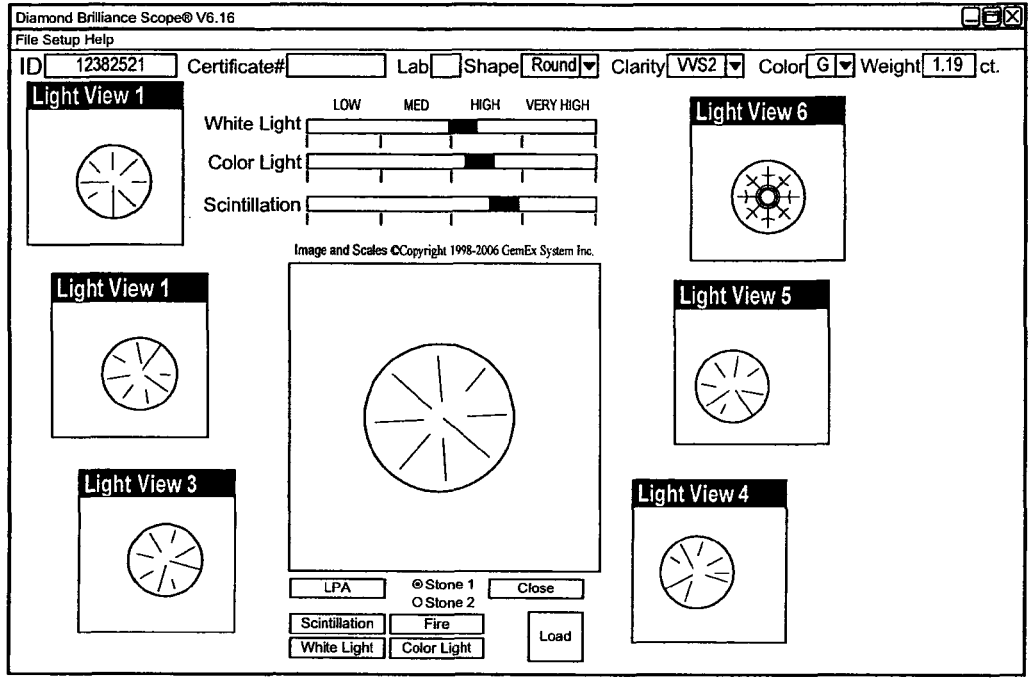
FIG. 2 is an illustration of exemplary Screen shots from a Gemex Light Performance analysis.
Figure 2:
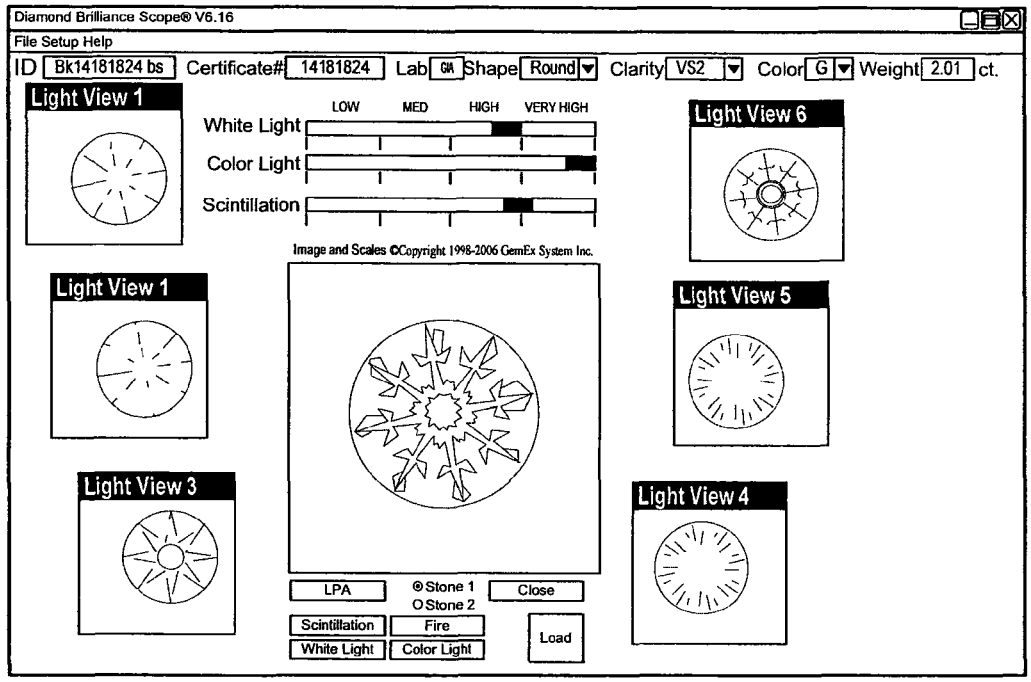

Once the universe of diamonds that may be used in the standardized basket have been culled using the above identified gemological standards, all of the diamonds will also be subject to the following optical requirements:

First, the diamonds must undergo a direct measurement of Light Performance. Using a Gemex Light Performance[1] analysis or similar light performance analysis the diamonds must score "High" or better on White Light, Color Light and Scintillation. A sample analysis is illustrated in FIG. 2.

[1] Gemex Light Performance is a proprietary system of optical analysis owned by Gemex Systems Inc. that is generally known in the industry.

Figure 3A:
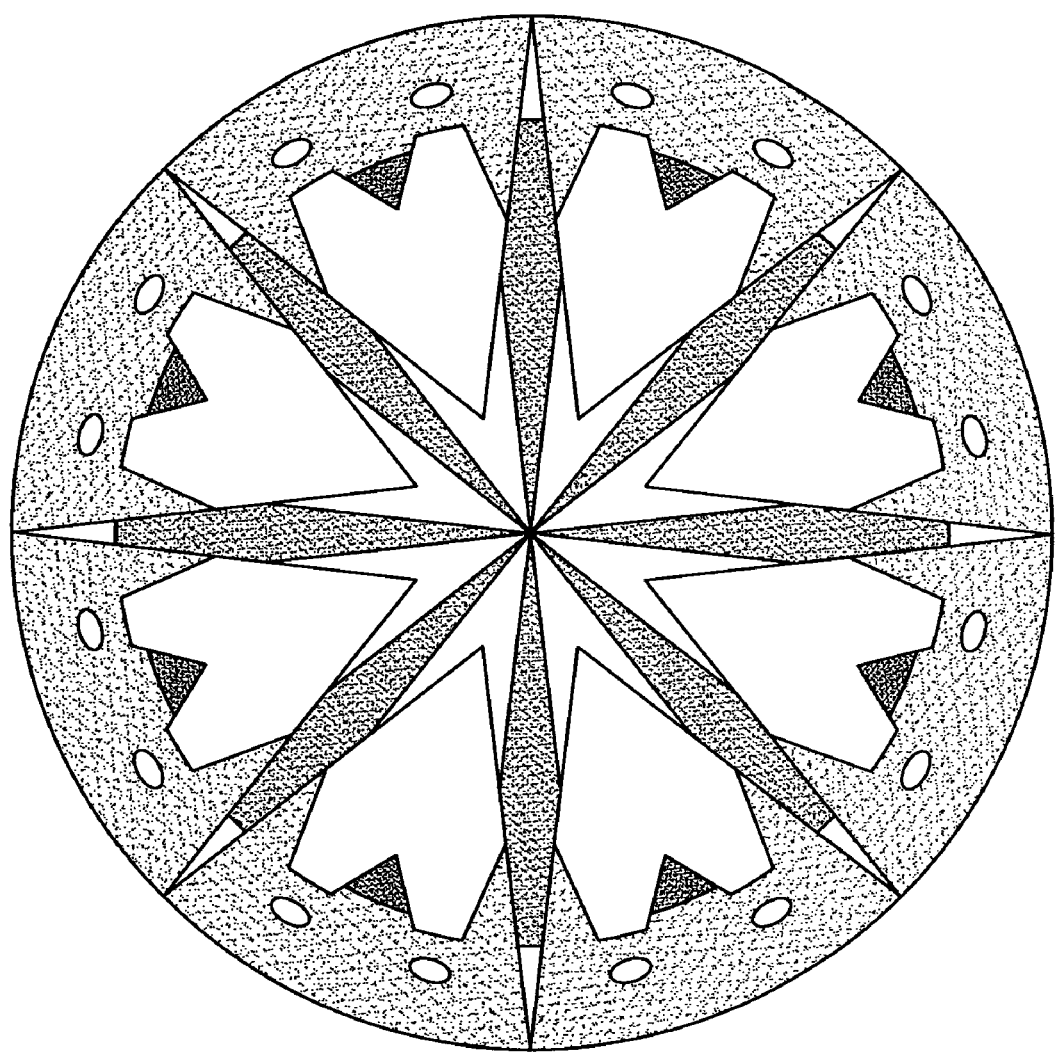
FIGS. 3A and 3B are illustrations of examples of the Hearts and Arrows that appear in a diamond that passes the optical symmetry analysis of the present invention illustrating the Hearts and Arrows that are visible.
Figure 3B:
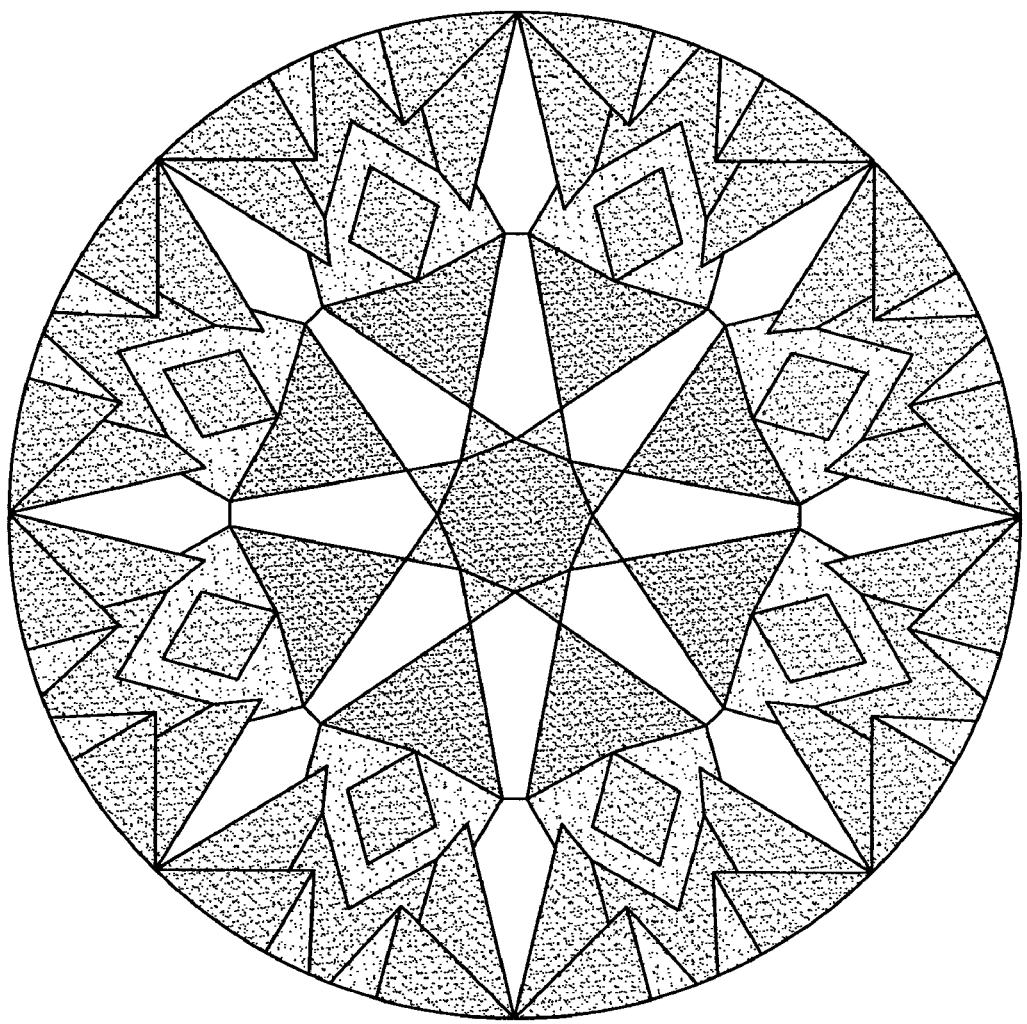
Figure 4A:
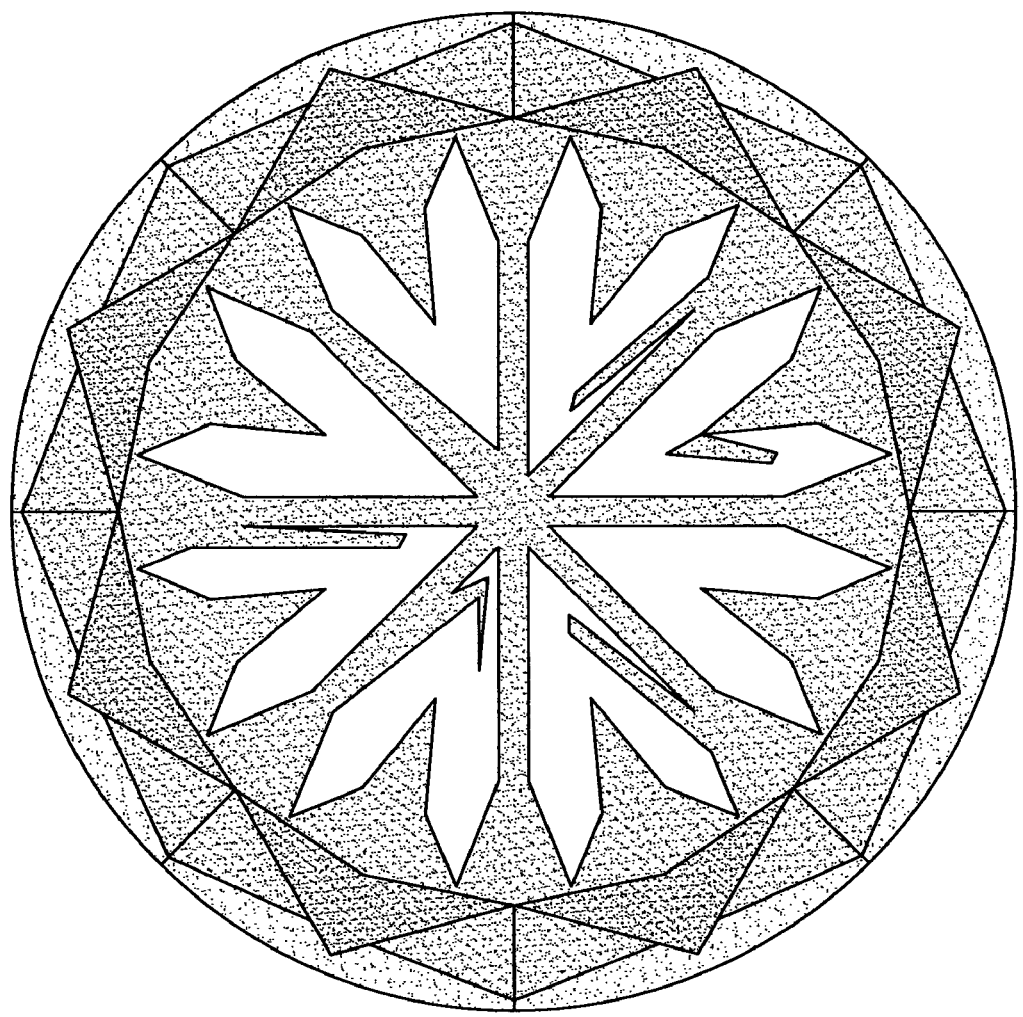
FIGS. 4A and 4B are an illustration of the Hearts and Arrows analysis of a diamond having the same gemological characteristics as FIGS. 3A and 3B, but which does not meet the Hearts and Arrows test.
Figure 4B:
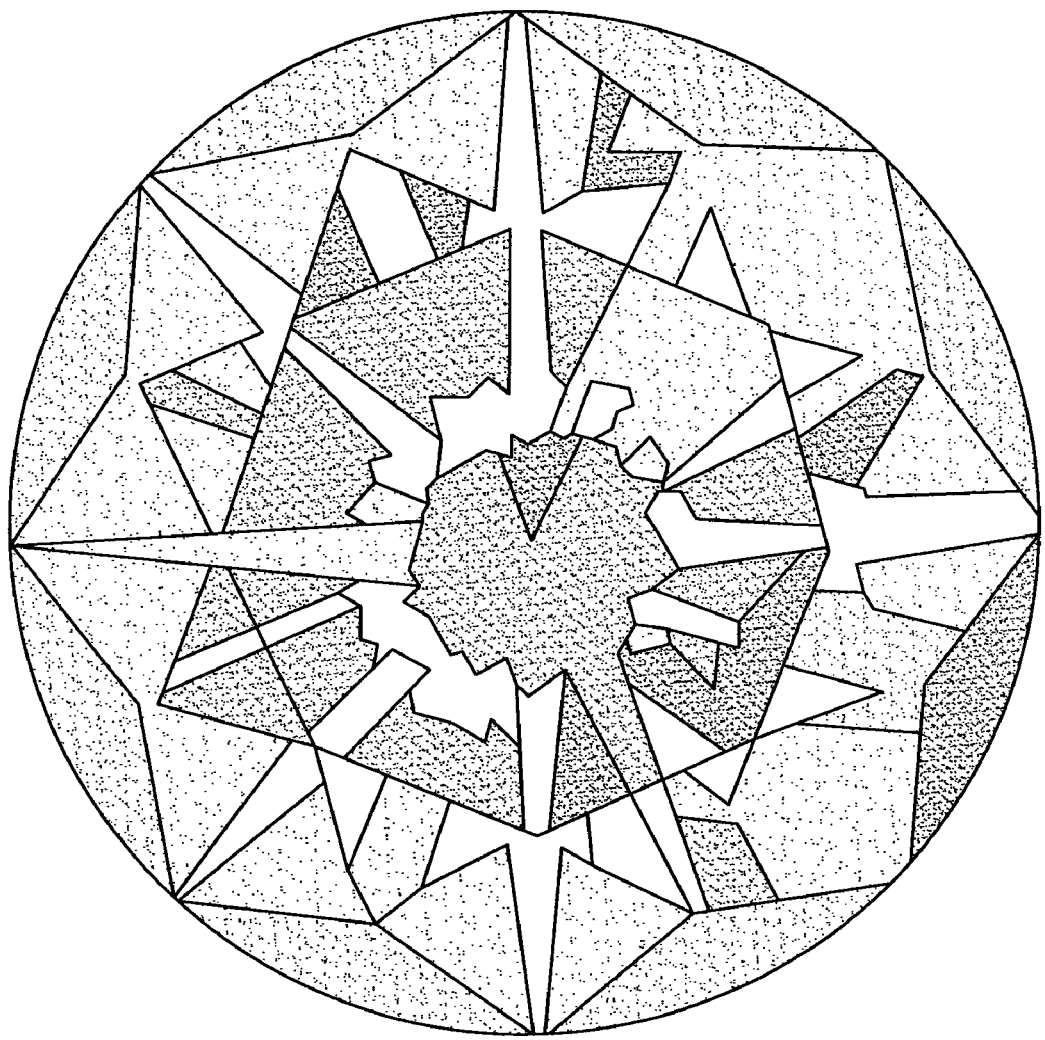

In addition, each diamond must meet the standard for optical symmetry. Each diamond must have excellent optical symmetry denoted by a "Hearts and Arrows" pattern when viewed through a Hearts and Arrow viewer. FIGS. 3A and 3B illustrate the Hearts and Arrows that appear in a diamond that passes the optical symmetry analysis. FIGS. 4A and 4B illustrate diamonds with identically graded gemological characteristics that do not meet the Hearts and Arrows test. Hearts are visible when viewing the diamond from its point down. Arrows are visible when viewing the gem diamond from its top down to the point. There is a significant difference between lab graded symmetry and optical symmetry that results in Hearts and Arrows. The Symmetry grade on a diamond's laboratory report only refers to external meet point symmetry (facet junctions meeting equally) and uniformity of the diamond's external shape. Optical Symmetry, on the other hand, is the type of symmetry that is seen through a Hearts and Arrows viewer (both crown and pavilion views) or an ideal-scope/ASET image (crown view). Optical Symmetry is the observable result of how the diamond's facets physically align with each other internally, and how light reflects inside the diamond. There are some grading systems that use the term optical symmetry as relating to external meet point symmetry only. Meet point symmetry is external and checks only junctions and crown/pavilion relations. This means a diamond can receive a grade of "Ideal" or "Excellent," but still have indexing issues, facet tilt, or yaw and extreme variations in angle measurements. These flaws are detected and diamonds are therefore eliminated using the present inventive method. Diamonds with this type of optical symmetry grading would not meet the requirement of the present invention.

Diamonds must also meet a light leakage requirement. To do so, the diamonds must have less than 20% blatant light leakage under Light Path Scope or Firescope inspection, sometimes referred to as reflector technology which is well known in the industry.

In addition, in the preferred embodiment, it is desirable although not absolutely required that the diamonds include Certificate of Warranties; Kimberly Process; and all vendors must certify that all diamonds supplied have non-conflict origins.

All diamonds supplied by all vendors must go through rigorous quality control inspections to insure that all requirement identified above have been met. Upon satisfactory approval in the preferred embodiment, all diamonds may be laser inscribed on their girdle "trading approved" or similar logo or seal such as GIGS™ (Global Investment Grade Standard™) along with an identification serial number for authentification purposes. Then they can be released to the market for trading purposes. It should be understood that while inscription is preferred, it is not necessary in order to be within the spirit and scope of the described invention.

As a result, all natural polished diamonds that conform to the classification of all the gemological and optical standards above are optically, aesthetically, technically and gemologically consistent (standardized). Even though each diamond is unique, the differences that separates them after having met the above gemological and optical standards are so minute that the very slight differences among them do not have any commercial significance nor monetary impact. Therefore, all diamonds that fall under a specific weight classification using the process described above are virtually indistinguishable in the commercial sense which enables them to be globally fungible and thus standardized. Just like coffee beans and soy beans where no soybean is exactly the same from nature, but can be grouped in terms of quality or graded for trading purposes, these diamonds can now be grouped together and traded.

While the diamonds that meet the requirements above are all capable of being used in a standardized basket, in the preferred embodiment of the present invention, the selection of diamonds are limited further. An example of how the diamonds can be limited further due to market factors is explained below.

FIGS. 5 and 6 are a sampling of commercially available diamonds that meet the gemological standards and the objective optical standards. From left to right for each carat weight diamond grouping, the sampling is broken down into the number of diamonds that fall within each color and clarity grouping. The next column to the right breaks the number of each diamond that fall into a particular grouping by color and clarity into a percentage of the whole sample. The blue and yellow shadings represent generally the most commercially available size categories. The third column illustrates the diamonds selected to be included in the standardized basket of diamonds. The fourth column in the series represents the dollar per carat weight value for each diamond that falls into the particular grouping based on clarity and color. The final column represents an approximation of the dollar value of each diamond selected to be included in the basket as well as a total value, carat weight and diamond quantity for each carat weight grouping ("Bundle"). In the examples in FIGS. 5 and 6, the basket is made up of 60 diamonds; however, any number of diamonds may be used to create a standardized basket depending on the overall desired value of the basket.

The primary objective is to achieve the maximum degree of fungibility that is acceptable for commercial commodity and financial trading of diamonds and requires the minimum effort for global diamond manufacturers to supply.

The first criterion considered in creating the exemplary standardized basket was weight class. Selection for the exemplary diamond basket was based on the 6 most commercially available size categories. Thus, the most abundant gems in supply are selected. Diamonds larger than the largest weight class of 2 ct are too scarce and too few. Diamonds smaller than 0.5 ct have a perception as being too small to be Investable Grade and more difficult to manage. Despite the perception as being too small, it is possible to use these sizes for purposes of the invention and for trading purposes because of the abundance of its supply. In addition, it would be within the spirit of the invention to have a basket that included very large diamonds, however, the supply would be limited.

The second criterion used in creating the exemplary standardized basket were quality color and clarity. The grouping of diamonds based on color quality and clarity was selected based on the most available of combinations so that the supply of diamonds is most available to satisfy the completion of the Diamond basket. Extremely rare combinations such as D Internally Flawless, DVVS1 and EVVS1 are excluded from this exemplary diamond basket (preferred embodiment) due to their limited availability. It should be understood that one using the described invention can create a Specialized Diamond Basket to trade these rare stones on a limited volume basis as well.

The next criterion used was cut and optical selection. This was already set to optimal standard according to the optical, proportion, finish, light performance and gemological requirements. Every diamond that is a part of the basket will conform to the defined cut standard. Therefore, all polished diamonds in the basket will exhibit such extreme similar light behavior and appearances that will render those having similar gemological pedigree with extraordinary homogeneity. Thus, by using the method described herein, a standardized fungible basket of diamonds has been created that can be traded in conjunction with financial instruments such as futures contracts, options, ETF much like corn or oil or other commodities are traded.

It is recognized that creating baskets with identically rated stones in each weight class may be difficult depending upon the commercial supply of diamonds or the increased expense of locating each particular size. For example a particular weight and particular color and clarity diamond that is part of the basket may turn out to be in short supply at a diamond supplier. As a result, an alternative embodiment of the standardized basket of diamonds could utilize diamonds that meet all the requirements of the method of the present invention, but that can appear slightly different due to its intrinsic color because its monetary value is equivalent to others in the unit.

Today, diamond values are set according to its 4C's. This allows diamonds of different Color, Clarity, Cut and Carat weight combination to arrive at equal monetary value. As an alternative to the standardized basket process identified above with respect to FIGS. 5 and 6, a value equivalent bundling scheme may be used. In the "Bundling" scheme, diamonds that have different color, clarity, carat weight but very similar monetary value can be bundled together so that they can be used interchangeably to fulfill the standardized diamond basket. This technique will substantially diminish the risk of running out of stock to fill creation orders. Within this scheme, a majority of the diamonds will visually appear the same to the ordinary person. This scheme also allows a more even spread of demand over a much broader range of color, clarity weight combination thus limiting a spike in value for any particular combination.

The requirement necessary for using the value equivalent bundle method include:

1. All diamond must be delivered at the minimum weight or higher;
2. All diamonds must be delivered at the set bundle color and clarity standard or higher (i.e., the previously described gemological and optical standards); and
3. All diamonds within the bundle must be valued in total no less than the set bundle value but can be higher.

Described below is an exemplary value equivalent bundle created using the following criteria:

1) Standardized basket=Creation Unit;
2) Each Creation unit is composed of 6 weight classes;
3) Each weight class is composed of specified Bundles of diamonds;
4). Each Bundle is created on a value equivalent concept;
5) Creation Unit minimum weight is 21.40 ct; and
6) Creation Unit=20 Diamonds or Pieces (PCs) Total.

Described below is the preferred make up of diamonds in each weight class for a basket of diamonds.

| Weight Range Per Weight Class | Number of Pieces Per Class | Total Weight Per Class | Quality Per Weight Class Per Bundle |
|---|---|---|---|
| .50-.059 ct | 3 PCs | 1.50 ct | Bundle A. GVS1(39.4) = 1 PC<br>Bundle B. HVS1(33.5) = 1 PC<br>Bundle C. HVS2(29.25) = 1 PC |
| .70-0.83 ct | 4 PCs | 2.80 ct | Bundle A. FVS2(48.8) = 1 PC<br>Bundle B. HVS2(42.8) = 2 PC<br>Bundle C. IVS2(37.8) = 1 PC |
| 1.00-1.19 ct | 5 PCs | 5.00 ct | Bundle A. GVS1(79) = 1 PC<br>Bundle B. HVS2(62) = 1 PC<br>Bundle C. IVS1(57) = 1 PC<br>Bundle D. GVS2(72) = 2 PC |
| 1.20-1.49 ct | 3 PCs | 3.60 ct | Bundle A. GVS1(80)<br>Bundle B. HVS2(62)<br>Bundle C. GVS2(72)<br>Bundle D. IVS1(57)<br>Options will be given for difficult sizes<br>Option #1 - 1 PC @ from Bundle A, B, C with no pairing option Group value = 256.8<br>Option #2 - 2 PC from Bundle C with pairing option and 1 PC from Bundle D with minimum weight of each stone 1.25 ct. Group value 251.25 (1.03 premium adjustment for size) |
| 1.5-1.75 ct | 3 PCs | 4.50 ct | Bundle A HSI1(74) = 1 PC<br>Bundle B GVS2(96) = 1 PC<br>Bundle C FVS1(11.7) = 1 PC |
| 2.00-2.39 ct | 2 PCs | 4.00 ct | Bundle A HVS1(12.3) = 2 PC<br>or<br>Bundle B GVS2(15.1) = 1 PC<br>IVS1(10.2) + 1 PC GVS2(15.1) |
| Totals = | 20 PCs | 21.40 ct min. | |

The number in the parenthetical represents a dollar per carat weight value.

In this example, total carat weight is selected as 21.40 ct. min. The calculation is set forth below:

Number of weight classes—6 in total: 0.50-0.59, 0.70-0.83 ct, 1.00-1.19, 1.20-1.49, 1.5-1.75, 2.00-2.39 ct.

Specific number of stones per class—0.50-0.059 ct-3 PCs, 0.70-0.83 ct-4 PCs, 1.00-1.19-5 PCs, 1.20-1.49-3 PCs, 1.5-1.753 PCs, 2.00-2.39 ct-2 PCs.

Weight per weight class—0.50-0.059 ct-3 PCs-1.50 ct.
Weight per weight class—0.70-0.83 ct-4 PCs-2.80 ct.
Weight per weight class—1.00-1.19 ct-5 PCs-5.00 ct.
Weight per weight class—1.20-1.49 ct-3 PCs-3.60 ct.
Weight per weight class—1.5-1.75 ct-3 PCs-4.50 ct.
Weight per weight class—2.00-2.39 ct-2 PCs-4.00 ct.
Grand Total=21.40 ct min.

In this example, every basket must weigh at least the minimum assured amount in total and in every weight class. Every basket can exceed the weight amount but cannot be less. The number of stones in each class is a constant and the total number of stones is also a constant (now set at 20 for the preferred embodiment, but other baskets may be made with a different number of stones. For example, you could have 40-stone standardized baskets).

Based on the bundle system, a value equivalent concept, diamond(s) with different gemological ratings in color and clarity (but which still meet the requirements of the inventive process) that have very similar monetary value, can be grouped in a single bundle. A unification of value for the diamonds over a range of quality and size will occur through actual large volume traded transactions. Those classified under this value bundle can be used interchangeably to satisfy the requirements of the basket. Certified vendors can provide any quality that is value higher than the bundle minimum value but never lower to complete unit.

Identified below are exemplary selections of diamonds for each weight class. Thus, looking at the ½ carat size weight class, under the preferred method, Bundle A would include a GVS1 (39.4) diamond. However, if that particular diamond meeting all the requirements of the present method is not available any of the following diamonds meeting all of the requirements of the inventive method: DVS2(41), EVS2(38), FVS1(40), GVS1(38) or HVVS1(40) may be substituted for the GVS1(39.4) diamond because they have an equivalent monetary value. The table below provides an example of value equivalent diamonds for each weight class that may be substituted to create a standardized basket.

½ Carat Size Weight Class Component Investable Grade Basket

Size Range=0.50-0.59 ct. Average minimum size=0.50. Quantity=3 pc. Total weight=1.50 ct.

Bundle A. GVS1(39.4)=DVS2(41), EVS2(38), FVS1(40), GVS1(38), HVVS1(40).

Bundle B. HVS1(33.5)=DSI1(35), GVS2(33), HVS1(33), IVVS1(33).

Bundle C. HVS2(29.25)=ESI1 (32), FSI1 (29), IVVS2 (30), HVS2(29), JIF(29).
Bundle GVS1=1 PC
Bundle HVS1=1 PC
Bundle HVS2=1 PC
*any diamond that is rating higher than the minimum requirement can be use as a substitute
**any diamond heavier than the required minimum weight can be use as a substitute
¾ Carat Size Weight Class Component Investable Grade Basket
Size Range=0.70-0.83 ct. Minimum size=0.70 ct.
Quantity=4 pc. Total weight=2.80 ct.
Bundle A. FVS2(48.8)=FVS2(47), EVS2(50), FVS1(51), GVS1(47), HVVS1(49), GVVS2(51), DSI1 (47).
Bundle B. HVS2(42.8)=ESI1(45), FSI1(42), GVS2(44), HVS1(42), HVS2(40), HVVS2(45), IVVS1(42).
Bundle C. IVS2(37.8)=IVS2(36), IVS1(38), IVVS2(40), GSI1(39), HSI1(36).
Bundle FVS2=1 PC
Bundle HVS2=2 PC
Bundle IVS2=1 PC
*any diamond that is rating higher than the minimum requirement can be use as a substitute
**any diamond heavier than the required minimum weight can be use as a substitute
1 Carat Size Weight Class Component Investable Grade Creation Unit
Size Range=1.00-1.19 ct. Minimum size=1.00 ct.
Quantity=5 pc. Total weight=5.00 ct.
Bundle A. GVS1(79)=EVS2(80), FVS2(77), GVS1(80), HIF(79).
Bundle B. HVS2(62)=FSI1(63), IVVS2(62), HVS2(62).
Bundle C. IVS1(57)=HSI1(57), JIF(57), IVS1(57), GSI1(59).
Bundle D. GVS2(72)=GVS2(72), HVVS2 (72), DVS1(99)+JVS2(47), DVS1(99)+ISI1(50) or EVS1(92)+IVS2(53), DSI1 1.03 ct or greater in weight.
Bundle A GVS1(80)=1 PC Group value=68.6×5.00 ct=343 min
Bundle B. HVS2(62)=1 PC
Bundle C. IVS1(57)=1 PC
Bundle D. GVS2(72)=2 PC
*any diamond that is rating higher than the minimum requirement can be use as a substitute
**any diamond heavier than the required minimum weight can be use as a substitute
***weight can be use to balance value
1.20 Carat Size Weight Class Component Investable Grade Basket
Size Range=1.20-1.49 ct. Average minimum size=1.20 ct @Quantity=3 pc. Total weight=3.60 ct.
Bundle A. GVS1(80)=EVS2(80), FVS2(77), GVS1(80), HIF(79)
Bundle B. HVS2(62)=FSI1(63), IVVS2(62), HVS2(62)
Bundle C. GVS2(72)=GVS2(72), HVVS2 (72), DVS1(99)+JVS2(47), DVS1(99)+ISI1 (50) or EVS1(92)+IVS2(53), DSI1(70) 1.25 ct or greater in weight
Bundle D. IVS1(57)=HSI1 (57), JIF (57), IVS1(57), GSI1(59)
*any diamond that is rating higher than the minimum requirement can be use as a substitute
**any diamond heavier than the required minimum weight can be use as a substitute
Options will be given for difficult sizes
Option #1—1 PC @from Bundle A, B, C (no pairing option) Group value=256.8
Option #2—2 PC from Bundle C with pairing option and 1 PC from Bundle D with minimum weight of each stone 1.25 ct. Group value 251.25 (1.03 premium adjustment for size)
1.50 Carat Size Weight Class Component Investable Grade Basket
Size Range=1.50-1.75 ct. Average minimum size=1.50 ct @Quantity=3 pc. Total weight=4.5 ct.
Bundle HSI1(74)=HSI1(74), IVS2(70)***, IVS1 (77), JVVS1(70), JVVS2(6700), JIF(73)
Bundle GVS2(96)=GVS2(96), DSI1 (95), HVVS1(96), ESI1(92)*, FSI1(87)*, HVVS2(92)*, HVS1(86)*
Bundle FVS1(11.7)=FVS1(11.7), DVS2(11.4)*, EVS2 (10.9)*, FVS2(10.4)*, GVS1(10.5)*, GVVS2 (11.3)*, GVVS1(11.8)*
Bundle HSI1(74)=1 PC Group value=817.65
Bundle GVS2(96)=1 PC
Bundle FVS1(117)=1 PC
*any diamond that is rating higher than the minimum requirement can be use as a substitute
**any diamond heavier than the required minimum weight can be use as a substitute
***weight can be use to balance value
2.00 Carat Size Weight Class Component Investable Grade Basket
Size Range=2.00-2.39 ct. Average minimum size=2.00 ct @Quantity=2 PCs. Total weight=4 ct.
Bundle IVS1(10.2)=IVS1(10.2), HSI1(10), IVS2(94)*, ISI1(87)*, JIF(95)*, JVVS1(91)*
Bundle HVS1(12.3)=HVS1(12.3), HVS2(11.5)*, GSI1 (11.2)*, FSI1(11.9)*, ESI1(12.3), IIF(11.6)*, IVVS1(11.3)***
Bundle GVS2(15.1)=GVS2(13.9), GVS1(15.2), GVVS2 (15.8), FVS2(15), EVS2(15.4), DVS2(16), HIF(14.8)
Bundle A. HVS1(12.3)=2 PC or
Bundle B. 1 PC IVS1(10.2)+1 PC GVS2(15.1)
***weight can be use to balance value FIG. 9 illustrates an exemplary basket made using the inventive method. In this example, the basket of diamonds have a cumulative value of approximate $174,000 or greater than $150,000. In addition, it is preferred that each standardized basket include 20 diamonds. It is expected that the total carat weight of each Basket will be a minimum of 21.40 carats. It should be understood that Baskets with a different stated number of diamonds and carat weight can be created using the inventive method described herein. It should also be understood that different classifications of diamonds and carat weight may be used to create Baskets that are within the spirit and scope of the described invention.

In another embodiment of the present invention, the standardized basket of diamonds may be used to create an Exchange-Traded Fund. It is expected that the standardized basket of diamonds can be used to create an Exchange-Traded Fund based on the basket of diamonds. (It should be understood that various ETF's may be created utilizing the different standardized baskets that are created using the inventive methods previously described. It should also be understood that the example is directed to an ETF based on a basket of diamonds, but that the ETF may be based on a basket of other gem stones or any combination thereof.) In this invention, the basket of diamonds is deposited with one or more custodians in exchange for a creation unit. The creation unit represents a plurality of shares of the Fund. In the preferred embodiment the number of shares in the creation unit is 20,000 shares. The number of shares of the creation unit can be selected to be any number, and may be selected to be more or less than 20,000 depending on the value of the creation unit and the target price range at which an individual share is expected to be sold.

The creation unit (i.e., the 20,000 shares) is provided to an Authorized Participant who may then sell the shares to clients and customers as an investment vehicle. The creation unit (i.e., all 20,000 shares) is redeemable for an amount of the commodity (i.e., the basket of diamonds and cash component) equal to the net asset value ("NAV") of the creation unit.

It is expected in the preferred embodiment of the invention that a Trust will issue GemShares (Shares) which represent units of fractional undivided beneficial interest in and ownership of the Trust. The Trust holds diamonds and is expected from time to time to issue Stock in exchange for deposits of diamond baskets and cash and to distribute diamond baskets and cash with redemption of Stock. In the preferred embodiment, a Creation Unit is a block of shares. As noted above, the number of shares in a Creation Unit may be determined by the Trustee. The Trust will issue and redeem Creation Units to certain Authorized Participants on an ongoing basis. Creation Units will be offered continuously at the NAV for shares on the day that an order to create a Creation Unit is accepted by the Trustee. The shares may be traded on any regulated exchange authorized by the Trust to trade the funds.

In the normal set up of a Grantor Trust of the type described herein, there is a Sponsor, Trustee, Custodian and, in some instances, a Marketing agent. It should be understood that a Grantor Trust is only one way in which the ETF would be marketed and sold. Other well-known formats or structures may be used, such as, by way of example, Publicly Traded Partnership or a 1940 Act structure.

The Sponsor is responsible for establishing the Trust and for the registration of the Shares. The Sponsor will generally oversee the performance of the Trustee and Trust's principal service providers, but will not exercise day-to-day oversight over the Trustee and such service providers.

The Trustee is generally responsible for the day-to-day administration of the Trust. That includes accessing interest from the cash component of the Creation Units to pay the Trust expenses; calculating the NAV of the Trust and the NAV per share;[2] receiving and processing orders from Authorized Participants to create and redeem Creation Units; coordinating the processing of such orders with the Custodian and the Depository Trust Company ("DTC"); and monitoring the Custodian.

[2] See below for the proprietary algorithm used to calculate the NAV.

The Custodian is responsible for the safekeeping of the Trust's diamond and cash collection deposited with it by Authorized Participants in connection with the creation of Baskets. The Custodian also facilitates the transfer of diamonds and cash in and out of the Trust through diamond accounts it will maintain for Authorized Participants and the Trust.

Figure 7:
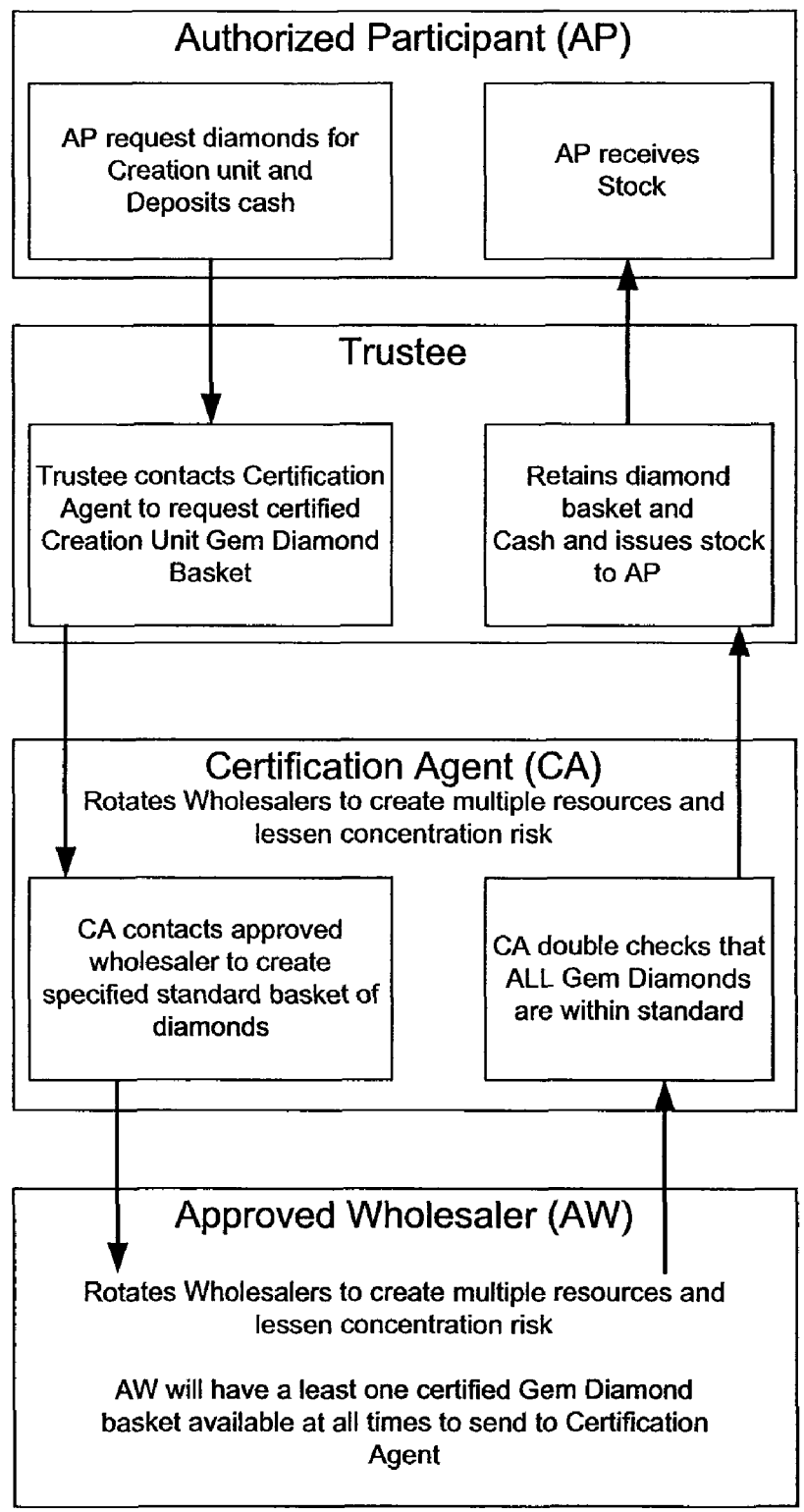
FIG. 7 is a flow chart of the Trust and the transactions associated with the sale and creation of the ETF made in accordance with the present invention.

The Marketing Agent will assist the Sponsor in developing a marketing plan for the Trust on an ongoing basis; preparing marketing materials regarding the Shares, executing the marketing plan for the Trust, providing market research in respect of diamonds, and reviewing the performance of the Trust. A description and flow chart of the Trust and the transactions associated with the sale and creation of the ETF is depicted in FIG. 7.

The diamond ETF would generally operate as follows:

When the Authorized Participant sees the demand from the market for more creation units the Authorized Participant will contact the Trustee and deposit cash to cover acquisition of a diamond basket and an additional specified cash component for the interest income component.

The Trustee will then contact the Certification Agent who will contact an Approved Wholesaler from the network of Approved Wholesalers. The Approved Wholesalers will deliver a certified Gem Diamond basket to the Certification Agent based on the Standard and will be paid by the Trustee.

The Certification Agent will again check that all Gem Diamonds meet the Standard. The certification Agent will deliver the certified Gem Diamond basket to the Trustee.

The Trustee will then issue ETF shares to the Authorized Participant. The Trustee will hold the Gem Diamonds and the cash component that make up each ETF creation unit.

The investment objective of the Trust is for the Shares to reflect the performance of the price of a standardized basket of diamonds, less the Trust's expenses plus interest. For many investors, the Shares will represent a cost effective investment relative to traditional means of investing in diamonds. As the value of the Shares is tied to the value of the diamonds held by the Trust, it is important in understanding the investment attributes of the Shares. The Shares are intended to offer investors a new and different opportunity to participate in the diamond market through an investment in a regulated securities market. Historically, the logistics of buying, storing and insuring diamonds have constituted a barrier to entry for institutional and retail investors alike. The Shares are intended to overcome these barriers to entry. The logistics of storing, insuring and evaluating the diamonds are dealt with by the Trustee and the related expenses are built into the price of the Shares.

The diamond collections are composed of diamonds that meet the gemological and optical standards described previously and cash. The cash component can be invested in a bank instrument such as a money market fund, or other interest bearing accounts. Keeping with the spirit of the invention, the cash component may be any amount. The purpose of the cash component is to provide interest to cover the expenses of the Trust and possibly provide dividends.

It should be understood that future contracts and options based on the standardized diamond Basket made in accordance with the methods described above are part of the invention. It should be understood that the ETF may also be structured based on the futures contracts. Future contracts on the diamond Baskets may be traded on exchanges such as the Chicago Mercantile Exchange ("CME"). Likewise, options for standardized diamond Baskets may be traded, for example, on the Chicago Board of Option Exchange ("CBOE").

The algorithm for the calculation of the diamond ETF intraday pricing and net asset value daily closing price will be based on a synergistic blend of a weighted average of the bid/offer midpoint of the most active front month diamond futures contract price, interest generated on a cash investment, the price demand for collection of diamonds meeting GemShares investment grade trading standards for natural polished diamonds designated specifications less fund expenses. The exemplary calculation process described herein references a 100 carat Basket. It should be understood that the calculation process described herein is applicable to any size standardized basket of diamonds that may be created using the inventive method described herein.

The diamond ETF net asset value pricing will be fixed Monday through Friday at 4:15 PM EST to be used as a reference point for new Creation and Redemption.

The diamond ETF pricing will be available during the market hours of the listed exchange. An example of the diamond ETF intraday pricing and net asset value daily closing price algorithm is described below:

$$\text{Intraday Pricing} = NAV = X_0(Y_0) + X_1(Y_1) + FI - FE$$

where
Intraday Pricing=Price of diamond ETF generated throughout the trading session.
NAV=Price of diamond ETF generated at the end of trading session.
$X_0$=calculation of the cash price from the futures price $$X_0 = X_f/[1 + r(t/365)]$$

$X_f$=most active front month futures contract price
r=current short term 30 day interest rates
t=number of days between futures trading date and futures expiry date
$X_1$=price for collection of diamonds meeting GemShare investment grade trading standards for natural polished diamonds specifications
$Y_0$ . . . =Weighting factor
FI=Fund Interest Income on US dollar cash deposit calculated on a daily basis
FE=Fund Expenses calculated on a daily basis
$X_0$=calculation of the cash price from the futures price
Calculate the diamond ETF price from the futures price on 31 Jan. 2008 using the March contract (expiry date Mar. 16, 2008)*.
The following information is applicable:
$X_f$=most active front month futures contract price=4,932.89*
r=domestic short term 30 day interest rates=3.50%*
Futures trading date=Jan. 18, 2008*
Futures expiry date=Mar. 27, 2008*
t=number of days between futures trading date and futures expiry date=70
Thus the cash price from the futures price will be:

$$X_0 = X_f/[1 + r(t/365)]$$

$$X_0 = 4,932.89*/[1 + (0.035 \times 70/365)]$$

$$X_0 = 4,932.89*/[1 + (0.035 \times 0.1918)]$$

$$X_0 = 4,932.89*/[1 + (0.006713)]$$

$$X_0 = 4,932.89*/[1.006713]$$

$$X_0 = 4,899.99*$$

$X_1$=price for collection of diamonds meeting Gem Share investment grade trading standards for natural polished diamonds specifications
$Y_0$ . . . =Weighting factors will be evaluated on a quarterly basis or as determined by the investment advisor. Weighting Factor Calculation:

Diamond futures contract size = 100 Carats*

Diamond futures front month March contract average price for January 1st thru 31st, 2008 = 4,900.00*

Diamond futures March contract average USD value for January 2008 = contract size (average price) = 100(4,899.99) = $489,999.00

Diamond futures March contract volume for 31 days in January =

50,000* contracts

-continued

Diamond futures average daily dollar value for January =

March contract average USD value for January 2008 (contract volume)

(percentage of contracts delivered – assume 1/2%) =

$489,999.00(50,000)(.005) = $122,499,750*

Diamond futures Average daily dollar value =

Diamond futures total dollar value for January/31 Days =

$122,499,750/31 Days = $3,951,604 per day*

Diamond cash market estimated daily value =

$65,000,000,000/year*/365 = $178,082,192/day

Weighting Factor for Diamond Futures Calculation =

Diamond Futures daily value/Diamond cash daily value =

$3,951,604 per day*/$178,082,192/day = .022

$Y_0$ = 0.022 Weighting Factor for Diamond Futures $Y_1$ = 0.978 Weighting Factor for Diamond cash market 1.000

FI = Fund Interest Income on US dollar cash deposit calculated on a daily basis

= Assume interest = 3.50%/year

= Interest Income = 3.50%/365 = $.009589 interest income/day

= $.009589 interest income/day

FE = Fund Expenses on a daily basis

= 55 basis points/year

= 55 basis points/365 days

= .000015 expenses/day

*Assumptions

Intraday Pricing = $NAV = X_0(Y_0) + X_1(Y_1) + FI - FE$

Intraday Pricing = NAV

= (Futures)(Weighting Factor) +
(Cash)(Weighting Factor) +
Fund Income – Fund Expenses Intraday Pricing = NAV

= ($489,999.00)(.022) +
(500,000.00)(.978) + .009589 – .000015

Intraday Pricing = NAV

= $10,779.98 + $489,000.00 + .009589 – .000015

Intraday Pricing = NAV = $499,779.99

An example of a base share price calculation is illustrated below. The price demand for collection of 100 Carats+ or −9 points diamonds meeting GEMEX and GIA designated specifications brought to Trustee for unit creation.

Intraday Pricing = NAV = $499,779.99*

Intraday Pricing = NAV / 20,000 shares

Intraday Pricing = $499,779.99* / 20,000 shares

= $24.99/share*

It should be apparent to those skilled in the art that the diamond baskets made in accordance with the present invention constitute an index such that it may be used in conjunction with a futures contract. For example, in the stock market, an index is a device that measures changes in the prices of a basket of shares, and represents the change using a single figure. Here, instead of shares, the basket is made up of a series of different sized diamonds selected by the inventive process. In this regard, the value of the basket of diamonds is the index and is intended to be reflective of the overall diamond market for investment grade diamonds. It should also be understood that although the example of the index is described in terms of a basket of diamonds, other gems may also be used to create indices and benchmarks.

An example of a diamond futures pricing algorithm and pricing calculation are described below. The algorithm for the calculation of the GemShares Diamond Index pricing is based on a arithmetic sum of a standardized gem diamond basket as previously defined in this patent application.

Diamond Futures Index Pricing=$X_f=X_0[1+r(t/365)]$ where $X_f$=most active front month futures contract price $X_0$=calculation of the cash price from the sum of Gem-Shares Diamond Index component diamonds meeting investment grade trading standards for natural polished diamonds r=current short term 30 day interest rates t=number of days between futures trading date and futures expiry date

EXAMPLE

Calculate the GemShares diamond futures price from the GemShares Diamond Index cash price on 31 Jan. 2008 assuming a March futures contract (expiry date Mar. 27, 2008)*.

$$X_f=X_0[1+r(t/365)]$$

$X_0$=calculation of the cash price sum of the Diamond Index component diamonds $X_0$=$49,955 (see Table 1 below)*

The following information is applicable:

r=domestic short term 30 day interest rates=3.50%*

Futures trading date=Jan. 18, 2008*

Futures expiry date=Mar. 27, 2008* t=number of days between futures trading date and futures expiry date=70

Thus the futures price will be:

$$X_f=X_0[1+r(t/365)]$$

$$X_f=49,955*[1+(0.035\times70/365)]$$

$$X_f=49,955*[1+(0.035\times0.1918)]$$

$$X_f=49,955*[1+(0.006713)]$$

$$X_f=49,955*[1.006713]$$

$$X_f=50,290.35*$$

TABLE 1

Example Diamond Index component diamonds

| | Qty | Weight | Value* |
|---|---|---|---|
| Weight Class I | | | |
| Bundle A | 1 | 0.53 | 2,279 |
| Bundle B | 1 | 0.55 | 1,980 |
| Bundle C | 1 | 0.52 | 1,716 |
| Class Total | 3 | 1.60 | 5,975 |
| Weight Class II | | | |
| Bundle A | 1 | 0.73 | 3,942 |
| Bundle B | 2 | 1.46 | 6,716 |
| Bundle C | 1 | 0.77 | 3,157 |
| Class Total | 4 | 2.96 | 13,815 |
| Weight Class III | | | |
| Bundle A | 1 | 1.01 | 7,777 |
| Bundle B | 1 | 1.02 | 8,874 |
| Bundle C | 1 | 1.03 | 7,004 |
| Bundle D | 1 | 1.05 | 6,510 |
| Class Total | 4 | 4.11 | 30,165 |
| Grant Total | 11 | 8.67 | 49,955 |

*Value is based on the current diamond wholesale trading system and does not necessarily include a cash component A diamonds futures deliverable using the standardized basket of the present invention would operate as follows:

The Certifying Agent checks for available "ready to trade inventory" with all Supplying Agents via real time data bases submitted by Supplying Agents through the Internet or other information technology platforms.

The Certifying Agent will deploy a range of highly efficient inventory procurement protocols to ensure the quickest and the most reliable assembly of components needed for the creation of a Diamond Basket. The Certifying Agent will have the option and discretion to either select all components of a basket from one Supplying Agent or several Supplying Agents.

A Supply Agent is an entity that provides the Certifying Agent with natural or synthetic diamonds that conform to the gemological, proportional, optical and institutional standards that are required for commodity trading purposes as described herein.

There are three basic types of Supplying Agents: Traditional Wholesales/Manufacturers—Diamond wholesalers/manufacturers that have been in the business of cutting and polishing diamonds for the current diamond market place. Typical delivery cycle from rough to finish to certification requires 60 to 90 days. Consolidators—Professionals that coordinate with networks of wholesalers/manufacturers to polish diamonds to the required standards for commodity trading purposes. Warehousing Investors—Any approved entity that invests capital to secure "ready to trade" diamond baskets that have met all requirements that are necessary for immediate deployment to the Trustee. They can be traditional wholesalers, manufacturers, sovereign states, miners or private investors. All approved investors are required to conform to all regulations and laws that might apply to this form of investing.

Certifying Agent proceeds to secure inventory to fulfill the Trustee's diamond baskets order by placing orders with appropriate Supply Agents.

Supplying Agent will either cut or gather diamonds with the sizes, gemological, proportional, optical standards (GemEx, Light Path Scope-leakage test, Hearts and Arrows-Optical symmetry) that will conform to the standards set for trading.

Supply Agent will proceed to Laser inscribe all diamonds with serial numbers or "Global Investment Grade Standard (GIGS) Supplying Agent logo" (for tracking purposes) that are approved by Supplying Agent to guarantee all require standards have been achieved.

All diamonds that will be submitted to the Certifying Agent must conform to all required standards and should have all official documentation that are required for trading.

Certifying Agent performs Quality Inspection of all diamond baskets delivered by Supply Agent Items that a Certifying Agent must inspect and verify before releasing to Trustee
- a. check carat weight
- b. check laser inscriptions
- c verify GIA certificate info and diamond plot
- d. validate color and clarity rating
- e. verify GemEx light performance data
- f. verify Hearts and Arrows optical symmetry
- g. verify Light leakage Quality Certifying Agent must provide a stamp of approval that assures the Trustee that all components of the baskets are correct, verified and authentic. This can be done with either a laser inscription or macro packaging document.

Certifying Agent must organize all documents and diamond baskets in a professional manner for Trustee to trade.

Certifying Agent must provide all tracking information required by security laws to the Trustee.

Trustee/Custodian receives diamond basket order from Certifying Agent and performs final Quality Control verification.

Trustee/Custodian team performs the same quality control inspection as the Certifying Agent.

Items that the Trustee must inspect and verify before releasing to the Exchange
- a. check carat weight
- b. check laser inscriptions
- c verify GIA certificate info and diamond plot
- d. validate color and clarity rating
- e. verify GemEx light performance data
- f. verify Hearts and Arrows optical symmetry
- g. verify Light leakage Quality Upon Trustee's approval of the diamond basket the Trustee must affix its stamp of approval on an inspection card/document on the approved date. Thus, the diamonds have proceeded through a triple verification procedure to insure compliance with the inventive process.

The diamond basket is now standardized, officially approved and certified. It can remain with the Trustee/Custodian until release to Exchanges for settlement/redemption delivery. The following is an example of an estimated diamond futures contract calculation:

Calculate the diamond futures price on 31 Jan. 2008 using the March contract (expiry date Mar. 16, 2008).*

The following information is applicable:
$X_f$=most active front month futures contract price
r=domestic short term 30 day interest rates=3.50%*
Futures trading date=Jan. 18, 2008*
Futures expiry date=Mar. 27, 2008*
t=number of days between futures trading date and futures expiry date=70
$X_0$=cash price Futures price $X_f$ will be:

$$X_f = X_0[1+r(t/365)]$$

$$X_f = 4,899.99*[1+(0.035 \times 70/365)]$$

$$X_f = 4,899.99*[1+(0.035 \times 0.1918)]$$

$$X_f = 4,899.99*[1+(0.006713)]$$

$$X_f = 4,899.99*[1.006713]$$

$$X_f = 4,932.88*$$

*Assumptions

While the inventive concepts have been described with respect to diamonds, it should be understood that the inventive concepts and methodologies are equally applicable to other gems such as rubies, emeralds, sapphires and in any combination. It should be understood that other baskets can be created using greater or lesser Standardized Weight Range Classes as described above. One skilled in the art can easily use the teachings and inventive concepts described herein to use gemological and optical standards to provide standardized baskets of other investable grade gems. While the invention has been described and illustrated with reference to specific embodiments, those skilled in the art will recognize that modifications and variations may be made without departing from the principles of the invention as described hereinabove and set forth in the following claims.

What is claimed is:

1. A system for generating an index/benchmark of investment grade diamonds intended to reflect the general market for investment grade diamonds comprising:
a collection of diamonds selected from a universe of diamonds, wherein the the collection of diamonds have predetermined gemologically similar characteristics;
predetermined distinct weight classifications; and
are optically substantially similar wherein each of the diamonds within a distinct weight classification has an equivalent monetary value;
an exchange for purchasing and selling financial instruments based on said collection of diamonds;
a computer with a data storage and processing capabilities for recording the prices at which said financial instruments based on said collection of diamonds are purchased and sold on said exchange and calculating the value of the collection of diamonds based on the recorded prices as a single figure, wherein the single figure is calculated by the computer using the using the following algorithm:

$$Index = NAV = X_o(Y_o) + Y_1(Y_1) + FI - FE.$$

2. The index of claim 1 wherein said monetary value is dependent in part upon the value of futures contracts for the delivery of said collection of diamonds.

3. The index of claim 1 wherein said index may form the basis for financial instruments.

4. The index of claim 3 wherein said financial instruments includes futures contracts, options, exchange traded funds, equities, or any other regulated or unregulated financial vehicle.

5. A system for trading a collection of gems as part of a financial instrument comprising:
fungible collection of gems including a plurality of gems having similar predetermined gemological characteristics; said plurality of gems each having a score of high or better on white light, color light, and scintillation using a Gemex Light Performance analysis or similar light performance analysis; each of said plurality of gems further being optically symmetrical as denoted by a hearts and arrow pattern when viewed through a hearts and arrow viewer; said plurality of gems having a pre-selected range of distinct weight classes, wherein each of the gems within each distinct weight class has an equivalent monetary value;

a financial instrument based upon the monetary value of said fungible collection of gems;

an exchange through which said financial instrument may be purchased and sold;

a computer having data storage and processing capabilities for recording and processing the purchases and sales of said financial instrument made through said exchange wherein said computer calculates the intraday pricing of said financial instruments based on said purchases and sales using the following algorithm:

Intraday pricing=NAV=$X_0(Y_o)+X_1(Y_1)+FI-FE$.

6. The fungible collection of gems of claim 5 wherein said gems are diamonds.

7. The fungible collection of gems of claim 6 wherein said predetermined gemological characteristics include predetermined gemological characteristics selected from the following: color, clarity, shape, cut grade, general properties, finish polish, symmetry, fluorescence, surface characteristics, and culet.

8. The fungible collection of gems of claim 7 wherein said pre-selected range of weight characteristics extends between about 0.5 carats to about 2.2 carats.

9. The fungible collection of gems of claim 6 wherein each of said plurality of gems have less than 20% blatant light leakage when analyzed using a blatant light leakage detection viewer such as a Firescope.

10. The invention of claim 6 wherein said financial instrument is an exchange traded fund.

11. The invention of claim 6 wherein said financial instrument is a futures contract.

12. The exchange traded fund of claim 11 wherein said predetermined gemological characteristics include predetermined gemological characteristics selected from the following: color, clarity, shape, cut grade, general properties, finish polish, symmetry, fluorescence, surface characteristics, and culet.

* * * * *